United States Patent [19]
Higashii et al.

[11] Patent Number: 5,539,115
[45] Date of Patent: Jul. 23, 1996

[54] PHENYLPYRIMIDINE DERIVATIVES, PROCESS FOR PREPARING THE SAME, LIQUID CRYSTAL COMPOSITION CONTAINING SAID DERIVATIVES AS ACTIVE INGREDIENT, AND LIQUID CRYSTAL ELEMENTS USING SUCH COMPOSITIONS

[75] Inventors: Takayuki Higashii, Takatsuki; Masayoshi Minai, Moriyama; Isao Kurimoto, Toyonaka; Shoji Toda, Ibaraki; Takeshi Tani, Tsukuba; Chizu Sekine, Tsukuba; Koichi Fujisawa, Tsukuba, all of Japan

[73] Assignee: Sumitomo Chemical Company, Limited, Osaka, Japan

[21] Appl. No.: 133,799

[22] Filed: Oct. 8, 1993

Related U.S. Application Data

[63] Continuation of Ser. No. 628,107, Dec. 17, 1990, abandoned.

[30] Foreign Application Priority Data

| Dec. 21, 1989 | [JP] | Japan | 1-333155 |
| Feb. 27, 1990 | [JP] | Japan | 2-48852 |
| Jun. 28, 1990 | [JP] | Japan | 2-171736 |
| Sep. 6, 1990 | [JP] | Japan | 2-238621 |
| Sep. 17, 1990 | [JP] | Japan | 2-248027 |

[51] Int. Cl.⁶ ............................................. C07D 239/26
[52] U.S. Cl. .................... 544/298; 544/315; 544/318; 544/335
[58] Field of Search .......................... 544/298, 318, 544/335, 315

[56] References Cited

U.S. PATENT DOCUMENTS 4,725,688  2/1988  Taguchi et al. ................... 544/298

FOREIGN PATENT DOCUMENTS

| 0255962 | 8/1987 | European Pat. Off. |
| 0255219 | 2/1988 | European Pat. Off. |
| 0294852 | 12/1988 | European Pat. Off. |
| 0347943 | 12/1989 | European Pat. Off. |
| 63-48270 | 2/1988 | Japan |
| 1301667 | 12/1989 | Japan |
| 2131444 | 5/1990 | Japan |

OTHER PUBLICATIONS

Terachi et al; Chemical Abstract, vol. 110, 1989 #223255c.
Terada et al; Chemical Abstract, vol. 111, 1989 #15487w.
Terachi et al., Chem. Abst. 110, 223255c, 1988.

*Primary Examiner*—Yogendra N. Gupta
*Attorney, Agent, or Firm*—Watson Cole Stevens Davis

[57] ABSTRACT

Disclosed in this invention are the phenylpyrimidine derivatives represented by the general formula I:

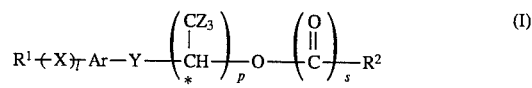

the alcohols represented by the formula:

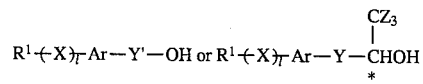

usable as starting material for the preparation of the phenylpyrimidine derivatives, and the processes for preparing such derivatives. The phenylpyrimidine derivatives of the formula I according to the present invention have very excellent properties as a liquid crystal compound and can be utilized effectively for the production of liquid crystal elements.

17 Claims, No Drawings

PHENYLPYRIMIDINE DERIVATIVES, PROCESS FOR PREPARING THE SAME, LIQUID CRYSTAL COMPOSITION CONTAINING SAID DERIVATIVES AS ACTIVE INGREDIENT, AND LIQUID CRYSTAL ELEMENTS USING SUCH COMPOSITIONS

This application is a continuation of application Ser. No. 07/628,107, filed Dec. 17, 1990 abandoned.

BACKGROUND OF THE INVENTION

1. Field of the Invention

This invention relates to the phenylpyrimidine derivatives useful as a principal component of ferroelectric liquid crystals or compositions thereof, a process for preparing such phenylpyrimidine derivatives, liquid crystal compositions containing said derivatives as active ingredient, and liquid crystal elements using such compositions.

2. Description of the Prior Art

Twisted nematic (TN) type display systems are most popularly used for the liquid crystal display elements at present. This TN liquid crystal display system has many advantages such as low driving voltage and small power consumption, but this type of display is inferior to the luminous type display devices such as cathode-ray tube display, electroluminescent display and plasma display in respect of response speed. A new TN type display device having the angle of twist regulated to the region of 180° to 270° has been developed, but this device is still unsatisfactory in response speed. Many efforts have been and are being made for the improvement of TN type displays, but there has yet been realized no TN type display element with satisfactorily high response speed. A possibility of a remarkable improvement of response time is noticed in the new display system using ferroelectric liquid crystals which are studied in earnest recently (Clark et al: Applid. Phys. Lett., 36, 899, 1980). This system makes use of a chiral smectic phase such as chiral smectic C phase (hereinafter referred to as Sc* phase) which exhibits ferroelectric characteristics. Sc* phase is not the only phase which shows ferroelectric characteristics; it is known that chiral smectic F, G, H and I phases also exhibit ferroelectric characteristics.

The ferroelectric liquid crystal material used for the practically applied ferroelectric liquid crystal elements is demanded to meet many property requirements. With the present state of the art, it is impossible to satisfy all of these requirements by use of a single compound; it is necessary to use a ferroelectric liquid crystal composition obtained by mixing several liquid crystal compounds or non-liquid-crystal compounds.

Beside the ferroelectric liquid crystal compositions composed of ferroelectric liquid crystal compounds alone, it is also reported that a ferroelectric liquid crystal composition can be obtained by using as base material a compound or composition presenting a non-chiral smectic C, F, G, H or I phase (hereinafter referred to as Sc phase, etc.) and mixing therewith one or more compounds assuming a ferroelectric liquid crystal phase (Japanese Patent Application Kokai (Laid-Open) No. 195187/86). There is also a report on the preparation of a ferroelectric liquid crystal composition by using as base material a compound or composition presenting a Sc phase, etc., and mixing therewith one or more compounds which are optically active but exhibit no ferroelectric liquid crystal phase (Mol. Cryst. Liq. Cryst., 89, 327, 1982).

Reviewing these teachings synthetically, it is noted that a ferroelectric liquid crystal composition can be formed by using as base material one or more optically active compound no matter whether they assume a ferroelectric liquid crystal phase or not. However it is desirable that the optically active substance used presents a liquid crystal phase, and even when it doesn't present a liquid crystal phase, it has structural analogy to a liquid crystal compound so that it may be called a quasi-liquid crystal material. There is yet found however no liquid crystal material which exhibits enough spontaneous polarization for enabling high-speed response, is low in viscosity and presents a ferroelectric liquid crystal phase in a wide range of temperature including room temperature region.

Some of the compounds according to the present invention are included in the concepts of Japanese Patent Application Kokai Nos. 49/89 and 301667/89 and EP 0255219, but these prior applications merely give a notional description of the preparation processes of said compounds and make no particular reference to said compounds.

Also, part of the compounds of this invention are included in the concept of Japanese Patent Application Kokai No. 131444/90, but this application gives no concrete description about the properties and other features of said compounds. Further, the conceptional preparation process of this patent lacks practical utility since it necessitates the troublesome reaction and steps and also uses as starting material a compound having asymmetric carbon atoms as starting material a compound having asymmetric carbon atoms for the introduction of asymmetric carbon atoms, so that this process can not be an industrially advantageous technique.

SUMMARY OF THE INVENTION

The present invention provides the phenylpyrimidine derivatives useful as a ferroelectric liquid crystal material or a component thereof which is specified by developing a sufficiently high degree of spontaneous polarization, being capable of high-speed response and presenting a ferroelectric liquid crystal phase in a temperature region around room temperature, and a process for preparing such phenylpyrimidine derivatives.

More specifically, the present invention concerns the phenylpyrimidine derivatives represented by the general formula I:

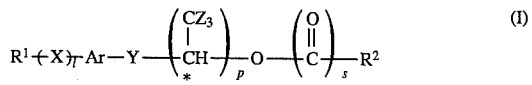

(wherein $R^1$ is a $C_{3-20}$ alkyl group; $R^2$ is a $C_{1-20}$ alkyl or $C_{2-20}$ alkoxyalkyl group which may be substituted with a halogen atom; X is —O—, —COO— or —OCO—; Ar is

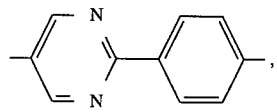

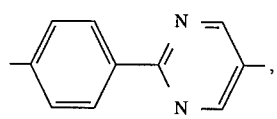

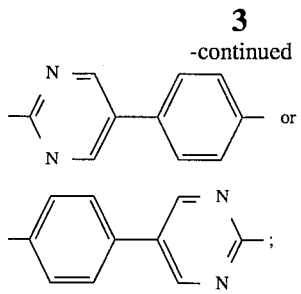 or

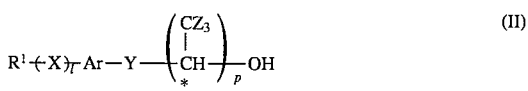

Y is $-(CH_2)_m$ or $-CH=CH-(CH_2)_n-$; Z is a hydrogen or fluorine atom; l, p and s are each a number of 0 or 1; m is an integer of 1–10 when Z is hydrogen atom and m is an integer of 0–10 when Z is fluorine atom; n is an integer of 0–8, but when p is 0, m is an integer of 2–10 and n is an integer of 1–8; and * mark denotes an asymmetric carbon atom), the intermediates for the synthesis thereof, a process for preparing said derivatives, liquid crystal compositions having said phenylpyrimidine derivatives as active ingredient, and liquid crystal elements using said compositions.

A detailed description of the present invention will be given below.

Among the phenylpyrimidine derivatives (I) according to the present invention, those of the formula I wherein s is 1 can be obtained by reacting the alcohols represented by the following formula II:

 (II)

(wherein $R^1$, X, Ar, Y, Z, l, p and * mark denote the same as defined above) with the carboxylic acids represented by the following formula III:

$$R^2COR' \quad (III)$$

(wherein $R^2$ has the same meaning as defined above, and R' is a hydroxyl group, $OCOR^2$ or a halogen atom).

In the above reaction between alcohol (II) and carboxylic acid (III), there can be used as the latter reactant the carboxylic acids of the formula III wherein $R^2$ is an alkyl group, and acid anhydrides or acid halides thereof such as acid chloride and acid bromide. These carboxylic acids may be either a racemate or of an optically active form.

The above reaction is generally carried out in the presence of a catalyst by using or without using a solvent.

In case of using a solvent in said reaction, such a solvent is selected from those which are inert to the reaction, for example, ethers, ketones, aliphatic or aromatic hydrocarbons, halogenated hydrocarbons and aprotic polar solvents, such as tetrahydrofuran, ethyl ether, acetone, methyl ethyl ketone, toluene, benzene, chlorobenzene, dichloromethane, dichloroethane, chloroform, carbon tetrachloride, dimethylformamide, hexane and the like. These solvents may be used either singly or in combination. The amount of the solvent used in the reaction is not specified.

In case of using an acid anhydride or an acid halide of an aliphatic carboxylic acid in the above reaction, the amount of such an acid anhydride or acid halide used in the reaction needs to be not less than one equivalent to the alcohol (II). Its upper limit is not specifically defined but preferably 1.1–4 equivalents to said alcohol (II).

As catalyst, there can be used the organic or inorganic basic substances such as dimethylaminopyridine, 4-pyrrolidinopyridine, triethylamine, tri-n-butylamine, pyridine, picoline, collidine, imidazole, sodium carbonate, sodium methoxide, and potassium hydrogencarbonate. It is also possible to use organic or inorganic acids such as toluenesulfonic acid, methanesulfonic acid, sulfuric acid and the like.

In use of such a catalyst, in case of using an acid halide of a carboxylic acid as starting material, pyridine or triethylamine is most preferably used.

The amount of the catalyst used is not defined as it is variable depending on the type of the acid anhydride or acid halide of a carboxylic acid used, its combination with the catalyst used and other factors, but in case of using an acid halide, the catalyst is used in an amount not less than one equivalent to the acid halide.

When using a carboxylic acid in the above reaction, it is possible to obtain a phenylpyrimidine derivative (s in the formula I is 1) by carrying out the dehydration and condensation reactions by using said carboxylic acid in an amount of usually 1–2 equivalents to the alcohol (II) in the presence of a condensation agent.

Carbodiimides such as N,N'-dicyclohexylcarbodiimide and N-cyclohexyl-N'-(4-diethylamino)cyclohexylcarbodiimide are preferably used as condensation agent in the above reaction. If necessary, an organic base such as 4-dimethylaminopyridine, 4-pyrrolidinopyridine, pyridine, triethylamine or the like may be used jointly with said condensation agent.

The amount of the condensation agent used is 1–1.5 equivalents to the carboxylic acid. In case of using an organic base jointly with said condensation agent, the amount of such an organic base used is 0.01–0.2 equivalent to the condensation agent.

Reaction temperature is usually in the range from −30° C. to 100° C., preferably from 0 to 80° C.

Reaction time is not specifically defined. The moment when the alcohol (II) used as one starting material has disappeared from the reaction system can be reckoned as the end point of the reaction.

By subjecting the resulting reaction mixture to the ordinary separating means such as extraction, liquid separation, concentration, etc., the objective phenylpyrimidine derivative (I) (s=1) can be obtained in a high yield. If necessary, the obtained product may be purified by further subjecting it to column chromatography, recrystallization or other suitable treatments.

The phenylpyrimidine derivatives of the formula 1 wherein s is 0 can be produced by reacting the alcohols of the above-shown formula II with an alkylating agent represented by the following formula IV:

 (IV)

wherein $R^2$ is as defined above, and Z represents a halogen atom or $-OSO_2R''$ wherein R'' is a lower alkyl group or a phenyl group which may be substituted.

The alkylating agent used in the above reaction is a halide or a sulfonic acid ester having a substituent $R^2$, and it can be produced from a corresponding alcohol by a known method.

The substituent $R^2$ in the alkylating agent (IV) may be an optically active group.

This reaction is usually carried out in the presence of a basic substance.

The amount of the alkylating agent (IV) used in the reaction can be arbitrarily determined provided that it is not less than one equivalent to the alcohol (II), but usually it is selected from within the range of 1 to 5 equivalents to the alcohol (II).

The above reaction is usually conducted in the presence of a solvent. The solvent used in the reaction is selected from those which are inert to the reaction, such as ethers, ketones, aliphatic or aromatic hydrocarbons, halogenated hydrocarbons and aprotic polar solvents, more specifically, tetrahydrofuran, ethyl ether, acetone, methyl ethyl ketone, toluene, benzene, chlorobenzene, dichloromethane, dichloroethane, chloroform, carbon tetrachloride, hexane, dimethylformamide, dimethyl sulfoxide, hexamethylphosphoramide, N-methylpyrrolidone and the like. These solvents may be used either singly or in combination. No particular restrictions are imposed on the amount of the solvent used in the reaction.

As basic substance, there can be used alkali metal hydrides such as sodium hydride and potassium hydride, alkali metals such as lithium, sodium and potassium, alkali metal alcoholates such as sodium ethylate and sodium methylate, alkali metal carbonates such as sodium carbonate and potassium carbonate, butyl lithium and the like. Such a basic substance needs to be added in an amount not less than one equivalent to the alcohol (II). The upper limit of the usable amount of said basic substance is not specifically defined, but usually it is 1.1–5 equivalents to said alcohol (II).

Reaction temperature is usually in the range from −50° C. to 120° C., preferably from −30° C. to 100° C.

Reaction time is not restricted. The moment of disappearance of the starting alcohol (II) from the reaction system may be regarded as the end of the reaction.

The resulting reaction mixture is subjected to the ordinary separating operations such as extraction, liquid separation, concentration, etc., for isolating the objective phenylpyrimidine derivative of the formula I (s=0) from the reaction mixture. If necessary, the product may be purified by column chromatography, recrystallization or other means.

In the above alkylating reaction, in case the substituent Z in the alkylating agent (IV) is iodine atom, silver oxide may be used in place of said basic substance. In this case, silver oxide needs to be used in an amount not less than one equivalent to the alcohol (II). The upper limit of the amount of silver oxide used in the reaction is not restricted but it is usually 5 equivalents to said alcohol (II).

When the alkylating reaction is carried out in the presence of silver oxide, the amount of the alkylating agent (IV) (Z=iodine atom) used in the reaction can be arbitrarily selected as far as it is not less than one equivalent to the alcohol (II). However it is preferred that the amount of the alkylating agent used is 2 to 10 equivalents to said alcohol (II).

As for the reaction solvent, it is possible to utilize the excess alkylating agent (IV) (Z=iodine atom) as solvent or to use those solvents which are inert to the reaction, such as ethers, ketones and hydrocarbons, more specifically, tetrahydrofuran, ethyl ether, dioxane, acetone, methyl ethyl ketone, benzene, toluene, hexane and the like, either singly or in combination.

Reaction temperature is usually in the range of 0° to 150° C., preferably 20° to 100° C.

Reaction time is usually in the range from one hour to 20 days.

Isolation of the objective phenylpyrimidine derivative (I) (s=0) from the reaction mixture can be accomplished by removing silver salts from the reaction mixture by filtration and subjecting the residue to the ordinary after-treatments such as extraction, liquid separation, concentration, etc. If necessary, the obtained product may be purified by column chromatography or other means.

The methods for obtaining phenylpyrimidine derivatives from alcohols (II) were described above. Listed below are the examples of substituent $R^2$ in the carboxylic acids (III) and alkylating agents (IV) used in the above-described methods: methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxybutyl, propoxyoctyl, propoxynonyl, propoxydecyl, butoxymethyl, butoxyethyl, butoxypropyl, butoxybutyl, butoxypentyl, butoxyhexyl, butoxyheptyl, butoxyoctyl, butoxynonyl, butoxydecyl, pentyloxymethyl, pentyloxyethyl, pentyloxypropyl, pentyloxybutyl, pentyloxypentyl, pentyloxyhexyl, pentyloxyheptyl, pentyloxyoctyl, pentyloxynonyl, pentyloxydecyl, hexyloxymethyl, hexyloxyethyl, hexyloxypropyl, hexyloxybutyl, hexyloxypentyl, hexyloxyhexyl, hexyloxyheptyl, hexyloxyoctyl, hexyloxynonyl, hexyloxydecyl, heptyloxymethyl, heptyloxyethyl, heptyloxypropyl, heptyloxybutyl, heptyloxypentyl, octyloxymethyl, octyloxyethyl, octyloxypropyl, decyloxymethyl, decyloxyethyl, decyloxypropyl, 1-methylethyl, 1-methylpropyl, 1-methylbutyl, 1-methylpentyl, 1-methylhexyl, 1-methylheptyl, 1-methyloctyl, 2-methylethyl, 2-methylbutyl, 2,3-dimethylbutyl, 2,3,3-trimethylbutyl, 2-methylpentyl, 3-methylpentyl, 2,3-dimethylpentyl, 2,4-dimethylpentyl, 2,3,3,4-tetramethylpentyl, 2-methylhexyl, 3-methylhexyl, 4-methylhexyl, 2,5-dimethylhexyl, 2-methylheptyl, 2-methyloctyl, 2-trihalomethylpentyl, 2-trihalomethyl-hexyl, 2-trihalomethylheptyl, 2-haloethyl, 2-halopropyl, 3-halopropyl, 3-halo-2-methylpropyl, 2,3-dihalopropyl, 2-halobutyl, 3-halobutyl, 4-halobutyl, 2,3-dihalobutyl, 2,4-dihalobutyl, 3,4-dihalobutyl, 2-halo-3-methylbutyl, 2-halo-3,3-dimethylbutyl, 2-halopentyl, 3-halopentyl, 4-halopentyl, 5-halopentyl, 2,4-dihalopentyl, 2,5-dihalo-pentyl, 2-halo-3-methylpentyl, 2-halo-4-methylpentyl, 2-halo-3-monohalomethyl-4-methylpentyl, 2-halohexyl, 3-halohexyl, 4-halohexyl, 5-halohexyl, 6-halohexyl, 2-haloheptyl, and 2-halooctyl. (In the above-shown examples of substituent $R^2$, "halo" signifies fluorine, chlorine, bromine or iodine.)

In the case of carboxylic acids (III), there can be further mentioned the following examples for substituent R2: halomethyl, 1-haloethyl, 1-halopropyl, 1-halobutyl, 1-halopentyl, 1-halohexyl, 1-haloheptyl, 1-halooctyl and the like.

These alkyl or alkoxyalkyl groups are either straight-chain or branched chain, and in the latter case they may be optical active groups.

Among the carboxylic acids having the above-shown substituents at $R^2$ in the formula III, the optically active ones can be obtained by oxidizing the corresponding alcohols or through reductive deamination of amino-acids. Some of these carboxylic acids occur naturally or can be derived from the optical active amino-acids or optical active oxyacids such as mentioned below which can be obtained by resolution.

Among the alkylating agents having said substituents $R^2$ the optical active ones can be easily produced from the corresponding alcohols in a known way. Some of said alcohols can be obtained from asymmetric reduction of the corresponding ketones with an asymmetric metallic catalyst or by use of a microorganism or an enzyme. Also, part of said alcohols occur naturally or can be derived from the optical active amino-acids or optical active oxyacids such as mentioned below which can be obtained by optical resolution: aniline, valine, leucine, isoleucine, phenylalanine, threonine, allothreonine, homoserine, alloisoleucine, tert-leucine, 2-aminobutyric acid, norvaline, norleucine, ornithine, lysine, hydroxylysine, phenylglycine, aspartic acid, glutamic acid, manderic acid, tropic acid, 3-hydroxybutyric acid, malic acid, tartaric acid, isopropylmalonic acid and the like.

Among the phenylpyrimidine derivatives represented by the formula I, those of the formula I wherein Y is $-(CH_2)_m$ and m is a number of 2° to 10 can be prepared by hydrogenating the phenylpyrimidine derivatives represented by the following formula I':

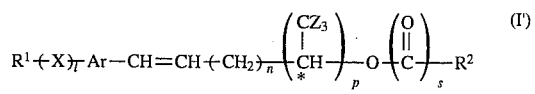
(I')

(wherein $R^1$ $R^2$, X, Ar, Z, l, n, p, s and * mark represent the same as defined above) by using hydrogen and a hydrogenating catalyst.

As the hydrogenating catalyst in the above reaction, Raney nickel or palladium type metallic catalysts are preferably used. Typical examples of such catalysts are palladium-carbon, palladium oxide, palladium black and palladium chloride.

Such a hydrogenating catalyst is used in an amount of usually 0.001° to 0.5 time, preferably 0.005 to 0.3 time by weight the phenylpyrimidine derivative of the formula I'. The reaction is conducted in a solvent. The solvent used for the reaction is selected from those inert to the reaction, which include water, hydrocarbons, alcohols, ethers, ketones, esters, halogenated hydrocarbons and amides, such as dioxane, tetrahydrofuran, methanol, ethanol, n-propyl alcohol, acetone, dimethylformamide, toluene, dichloromethane and ethyl acetate. These solvents may be used either singly or in combination.

The reaction is conducted under normal hydrogen pressure or under a pressurized state of hydrogen. It is desirable that the moment when the absorption of hydrogen has just become 1.0 equivalent to the starting phenylpyrimidine derivative of the formula I' be counted as the end point of the reaction.

The reaction is performed at a temperature in the range from −10° C. to 100° C., preferably from 10° C. to 60° C.

After the reaction, the reaction mixture is cleared of the catalyst by filtration or other means and then subjected to the appropriate after-treatments such as concentration to give the objective phenylpyrimidine derivative of the formula I in which Y is $-(CH_2)_m$ and m is an integer of 2 to 10. This product may be purified as desired by suitable means such as column chromatography or recrystallization.

The alcohols of the formula II used as one starting material in the reaction according to the present invention can be synthesized from the following processes.

(1) When p in the formula II is 1:

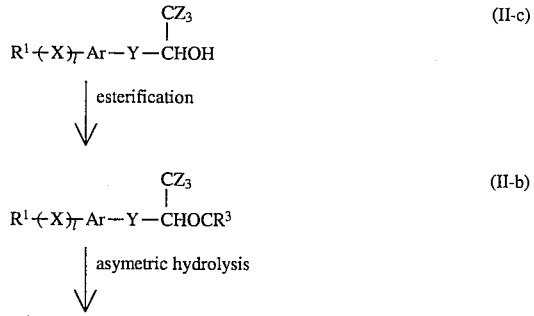

(II-a)

(In the above formulae, $R^1$, X, Ar, Y, Z, l and * mark signify the same as defined above, and $R^3$ represents a lower alkyl group.)

As for the method for the synthesis of the compounds represented by the formula II-b or II-c, in case Y in the formula is $-(CH_2)_m$ or $-CH=CH-(CH_2)_n$ (wherein m is an integer of 2 to 10 and n is an integer of 0 to 8), said compounds can be synthesized from the following process:

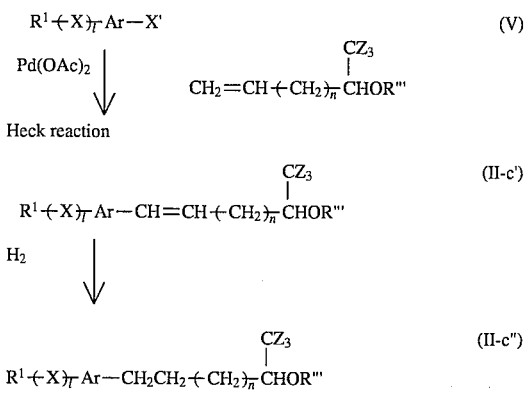

(In the above formulae, $R^1$, X, Ar, Z, l and n are as defined above, R'" represents hydrogen atom or lower alkyl group, and X' represents bromine or iodine atom.)

In case R'" in the formula II-c' or II-c" is a lower acyl group, these compounds may be hydrolyzed and used as alcohols represented by the formula II-c.

In case Y is $-(CH_2)_m$ (wherein m is 0 or said compounds can be synthesized from the following process:

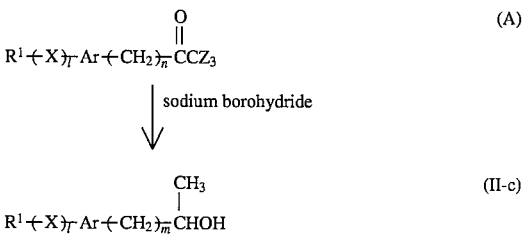

The above starting compound (A) can be synthesized from the following reaction when Ar is

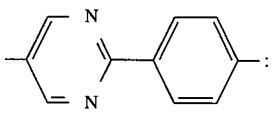:

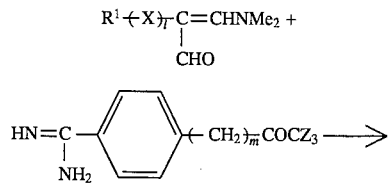

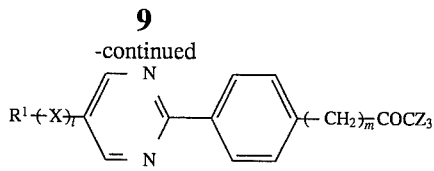

(2) When p is 0 and Y is $-(CH_2)_m$ or $-CH=CH-(CH_2)_n$ (wherein m is an integer of 3–10 and n is an integer of 1–8):

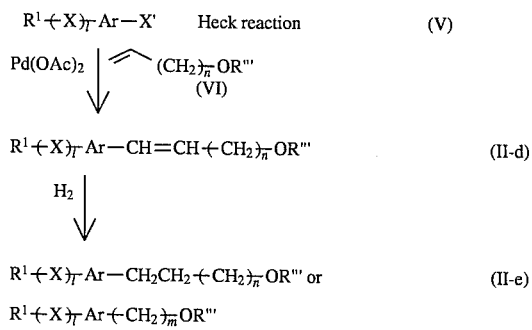

(In the above formulae, $R^1$, X, Ar, l, m and n denote the same as defined above, R''' is hydrogen atom or lower acyl group, and X' is bromine or iodine atom.)

In case R''' in the formula (II-d) or (II-e) is a lower acyl group, the compound is hydrolyzed and used as a corresponding alcohol.

(3) When p is 0 and Y is $-(CH_2)_m$ (wherein m is 1 or 2):

The desired alcohol can be synthesized from the following reaction when Ar is

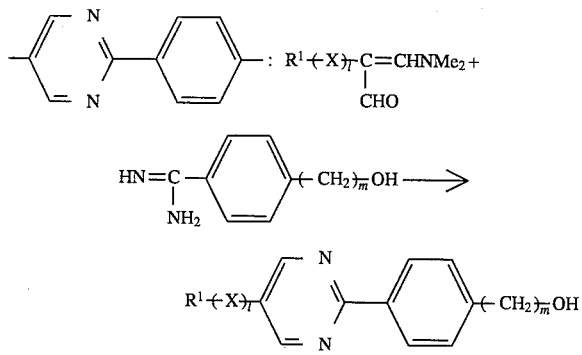

(In the above formulae, $R^1$, X, Ar, m and l are as defined above.)

The synthesis of a compound of the formula II-a from a compound of the formula II-b can be effectuated by subjecting the compound of the formula II-b to asymmetric hydrolysis by using an esterase having the ability to hydrolyze one of the enantiomers of the compound of the formula II-b.

When the term "esterase" is used in the present specification, it means esterase in its broad sense which includes lipase.

As the microorganism for producing an esterase used in this reaction, there can be used all types of microorganisms which are capable of producing an esterase having the ability to asymmetrically hydrolyze the esters.

Examples of such microorganisms are those belonging to the genera Enterobacter, Arthrobacter, Brevibacterium, Pseudomonas, Alcaligenes, Micrococcus, Chromobacterium, Microbacterium, Corynebacterium, Bacillus, Lactobacillus, Trichoderma, Candida, Saccharomyces, Rhodotorula, Cryptococcus, Torulopsis, Pichia, Penicillium, Aspergillus, Rhizopus, Mucor, Aureobasidium, Actinomucor, Norcardia, Streptomyces, Hansenula, and Achromobacter.

Cultivation of these microorganisms can be usually accomplished according to the conventional methods, and a liquid culture can be obtained by performing liquid incubation.

For example, a microorganism is inoculated into a sterilized liquid medium [a malt extract/yeast extract medium (prepared by dissolving 5 g of heptone, 10 g of glucose, 3 g of malt extract and 3 g of yeast extract in 1 liter of water, with pH adjusted to 6.5) for mold and yeasts and a sweetened bouillon medium (prepared by dissolving 10 g of glucose, 5 g of peptone, 5 g of meat extract and 3 g of NaCl in 1 liter of water, with pH adjusted to 7.2) for bacteria] and subjected to reciprocal shaking culture usually at 20°–40° C. for 1–3 days. If necessary, solid culture may be employed.

Some of the esterases of microbial origin are commercially available. Examples of such commercially available esterases are Lipase P (lipase of the genus Pseudomonas, available from Amano Pharmaceutical Co., Ltd.), Lipase AP (lipase of the genus Aspergillus, available from Amano Pharmaceutical Co., Ltd.), Lipase M-AP (lipase of the genus Mucor, available from Amano Pharmaceutical Co., Ltd.), Lipase MY (lipase of *Candida cylindlasse*, available from Meito Sangyo Co., Ltd.), Lipase PL (lipase of the genus Alcaligenes, available from Meito Sangyo Co., Ltd.), Lipase AL (lipase of the genus Achromobacter, available from Meito Sangyo Co., Ltd.), Lipase Godo BSL (lipase of the genus Arthrobacter, available from Godo Shusei Co., Ltd.), lipase of the genus Chromobacterium (available from Toyo Brewage Co., Ltd.), Talipase (lipase of *Rhizopus delemer*, available from Tanabe Pharmacetical Co., Ltd.), and Lipase Saiken (lipase of the genus Phizopus, available from OSAKA Bacteria Research Institute).

It is also possible to use animal and vegetable esterases such as steapsin, pancreatin, swine lever esterase and wheat germ esterase.

Used as esterase in this reaction is an enzyme obtained from animals, plants or microorganisms, and it can be used in various forms such as purified enzyme, crude enzyme, enzyme-containing matter, liquid culture of microorganism, culture, cells, culture filtrate and the treated substances thereof. An enzyme-microorganism combination is also usable. Further, fixed enzymes or fixed cells formed by fixing the enzymes or cells to a resin or the like can be used.

Said asymmetric hydrolysis reaction is carried out by vigorously stirring a mixture of a starting compound (II-b) and an enzyme or microorganism such as mentioned above, usually in a buffer solution.

As buffer solution, there can be used the ordinarily employed buffer solutions of the salts of inorganic acids such as sodium phosphate and potassium phosphate or the salts of organic acids such as sodium acetate and sodium citrate. The pH of the buffer solution is preferably in the range of 8 to 11 in case of using a culture of an alkalophilic bacterium or an alkaline esterase and 5 to 8 in case of using a culture of a non-alkalophilic microorganism or an esterase having no alkali resistance. The concentration of the buffer solution is usually in the range of 0.05 to 2M, preferably 0.05 to 0.5M.

Reaction temperature is usually 10° to 60° C., and reaction time is generally 10 to 70 hours. They are not restricted to these ranges.

In case of using a lipase belonging to the genus Pseudomonas or Arthrobacter in said asymmetric hydrolysis reaction, there can be obtained an optical active compound (II-a) with a relatively high optical purity.

In the practice of said asymmetric hydrolysis reaction, an organic solvent inert to the reaction such as toluene, chloroform, methyl isobutyl ketone, dichloromethane and the like can be used in addition to the buffer solution. Use of such a solvent is conductive to advantageous execution of the asymmetric hydrolysis reaction.

As a result of said asymmetric hydrolysis reaction, only one of the enantiomers of the starting compound (II-b) is hydrolyzed to form a compound (II-a), while the optical active ester constituting the other enantiomer of the starting compound (II-b) remains unhydrolyzed.

After said hydrolysis reaction, the reaction solution is extracted with a suitable solvent such as methyl isobutyl ketone, ethyl acetate, ethyl ether or the like, then the solvent is evaporated away from the organic layer and the concentrated residue is column-chromatographed or otherwise treated to separate the optical active compound (II-a) which is the hydrolyzate and the unhydrolyzed optical active ester (unhydrolyzed enantiomer of the starting compound (II-b)).

If desired, the optical active ester obtained here may be hydrolyzed to form an optical active compound (II-a) which is the antipode of the previously obtained optical active alcohol.

For synthesizing a compound of the formula II-b from a compound of the formula II-c, the latter compound is reacted with a carboxylic acid represented by the formula VIII:

$$R^3COOH \qquad (VIII)$$

(wherein $R^3$ is a lower alkyl group) or a derivative thereof.

As the lower alkylcarboxylic acid (said carboxylic acid (VIII) or a derivative thereof) serving as acylating agent in the above acylating reaction, there are usually used the acid anhydrides or acid halides of the lower alkylcarboxylic acids, such as acetic anhydride, propionic anhydride, acetic acid chloride or bromide, propionic acid chloride or bromide, butyl chloride or bromide, valeroyl chloride or bromide, and the like.

The reaction between a compound (II-c) and a lower alkylcarboxylic acid is conducted under the ordinary esterification conditions by using a catalyst in the presence or absence of a catalyst.

In case of using a solvent in this reaction, such a solvent is selected from those which are inert to the reaction, such as aliphatic or aromatic hydrocarbons, ethers, ketones, halogenated hydrocarbons and aprotic polar solvents, more specifically, tetrahydrofuran, ethyl ether, acetone, methyl ethyl ketone, toluene, benzene, chlorobenzene, dichloromethane, dichloroethane, chloroform, carbon tetrachloride, dimethylformamide, hexane and the like. These solvents may be used either singly or in combination. The amount of the solvent used in the reaction is not specifically restricted.

The amount of the lower alkylcarboxylic acid (VIII) used in the above reaction needs to be not less than one equivalent to the starting compound (II-c). Its upper limit is not specifically defined but preferably 1.1–4 equivalents to said compound (II-c).

As catalyst in the above reaction, there can be used organic and inorganic basic substances such as dimethylaminopyridine, triethylamine, tri-n-butylamine, pyridine, picoline, imidazole, sodium carbonate, sodium methylate, potassium hydrogencarbonate and the like. The amount of the catalyst used in the reaction is not definitely determined, but usually the catalyst is used in an amount of 1 to 5 equivalents to the compound (II-c).

In case of using an organic amine as solvent, such an amine may serve as a catalyst, too.

Acids such as toluenesulfonic acid, methanesulfonic acid, sulfuric acid and the like are also usable as catalyst.

The amount of the catalyst used in the reaction can not be specified as it is variable depending on the type of the lower alkylcarboxylic acid used, its combination with the catalyst used and other factors, but in case of using an acid halide as the lower alkylcarboxylic acid, the catalyst should be used in an amount not less than one equivalent to said acid halide.

Reaction temperature is usually in the range from –30° C. to 100° C., preferably from –20° C. to 90° C.

Reaction time is not specifically defined. The moment of disappearance of the starting compound (II-c) from the reaction system may be taken as the end point of the reaction.

After the reaction, the reaction mixture is subjected to the ordinary separating treatments such as extraction, liquid separation, concentration, recrystallization, etc., whereby a compound of the formula II-b can be obtained in a high yield. If necessary, the obtained compound may be purified by column chromatography or other means. The reaction mixture can be used in the form as it is in the next step. wherein Y is $-(CH_2)_{\overline{m}}$ and m is an integer of 2 to 10

The optical active compounds of the formula II-a can be produced by hydrogenating the optical active unsaturated alcohols represented by the following formula II-a':

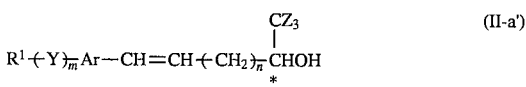

(wherein $R^1$, Y, Ar, Z, n and * mark denote the same as defined above) by using hydrogen and a hydrogenation catalyst.

In the above reaction, Raney nickel or palladium type metallic catalysts such as palladium-carbon, palladium oxide, palladium black and palladium chloride are preferably used as hydrogenation catalyst. Such a hydrogenation catalyst is used in an amount of usually 0.001 to 0.5 time, preferably 0.005 to 0.3 time by weight the optical active unsaturated alcohol (II-a'). The reaction is carried out in a solvent. The solvent used in this reaction is selected from those which are inert to the reaction, such as water, hydrocarbons, alcohols, ethers, ketones, esters, halogenated hydrocarbons and amides, more specifically, dioxane, tetrahydrofuran, methanol, ethanol, n-propyl alcohol, acetone, dimethyl formamide, ethyl acetate and the like.

The above reaction is conducted under normal hydrogen pressure or under a pressurized state of hydrogen, and preferably the time when the absorption of hydrogen became 1–1.2 equivalent to the starting optical active unsaturated alcohol (II-a') is presumed as the end point of the reaction. The reaction is performed at a temperature in the range of –10° to 100° C., preferably 10 to 60° C.

After the reaction, the catalyst is removed from the reaction mixture by filtration or other means and the residue is subjected to the after-treatments such as concentration to obtain the objective compound. If necessary, the product may be purified by recrystallization, column chromatography or other means.

There can be likewise produced the compounds of the formula II-b wherein Y is $-(CH_2)_{\overline{m}}$ and m is an integer of 2 to 10.

Here, the Heck reaction conducted in the preparation of the compounds (II-c') or (II-d) is explained in greater detail.

The compounds represented by the formula II-c' or II-d can be obtained by reacting the halides represented by the formula V with the olefins represented by the following formula VI:

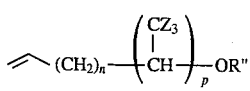

(wherein R''' and p represent the same as defined above, and n is an integer of 1 to 8 when p is 0 and 0 to 8 when p is 1) in the presence of a metallic catalyst and a basic substance.

The starting compounds of the formula V and VI can be prepared according to the methods shown in the prior art literature.

The amount of the olefin (VI) used in the above reaction is usually 0.9–10 equivalents, preferably 1–2 equivalents to the halide (V).

As the metallic catalyst in the above reaction, there can be used the palladium type catalysts such as palladium chloride, palladium acetate, triphenylphosphinepalladium complex, palladium-carbon and the like as well as the nickel and rhodium type catalysts.

The amount of the metallic catalyst used in the reaction is in the range of $10^{-3}$ to $10^{-1}$ equivalent to the starting halide (V).

In the above reaction, it is necessary to use, beside said metallic catalyst, a trivalent phosphorus or arsenic compound as co-catalyst. Such a compound is selected from those represented by the following formula VII:

(wherein M is phosphorus or arsenic atom, and $R^4$, $R^5$ and $R^6$ may be the same or different from each other and represent alkyl group, aryl group, alkoxy group, aryloxy group or halogen atom), the typical examples thereof being tri-n-butylphosphine, triphenylphosphine, tri-o-tolylphosphine, tri-o-tolyl phosphite, phosphorus trichloride, and triphenylarsenic.

The amount of such a phosphorus or arsenic compound used as co-catalyst in the above reaction is 0.5–50 equivalents, preferably 10–30 equivalents to said metallic catalyst.

As basic substance, there can be used the carbonates, carboxylates, alkoxides and hydroxides of alkali metals and the organic bases. It is, however, preferred to use tertiary amines or carbonates of alkali metals such as triethylamine, di-isopropylethylamine, tri-n-butylamine, tetramethylethyleneamine, dimethylaniline, sodium carbonate, sodium hydrogencarbonate and the like.

The amount of the basic substance used in the reaction is 1–5 equivalents to the halide (V).

If necessary, acetonitrile, tetrahydrofuran, dimethylformamide, hexamethylphosphorylamide, N-methylpyrrolidone, methanol or like substance may be used as reaction solvent. Its amount used in the reaction is not specifically defined.

This reaction is usually performed in an inert gas such as nitrogen gas and argon gas.

In the process of the present invention, the yield of the objective compound (II-d) or (II-c') can be enhanced by raising the reaction temperature, but since a too high temperature causes increase of the by-products, the reaction is usually carried out at a temperature in the range of 15° to 190° C., preferably 100° to 150° C.

After the reaction, the reaction mixture is subjected to the ordinary after-treatments such as extraction, distillation, recrystallization, etc., to give the objective compound (II-d) or (II-c').

Listed below are the examples of the phenylpyrimidine derivatives represented by the formula I which were obtained according to the processes described above:

5-($C_{3-20}$ alkyl)-2-(4-substituted phenyl)pyrimidine,
2-($C_{3-20}$ alkyl)-5-(4-substituted phenyl)pyrimidine,
5-($C_{3-20}$ alkyl)oxy)-2-(4-substituted phenyl)pyrimidine,
2-($C_{3-20}$ alkyl)oxy)-5-(4-substituted phenyl)pyrimidine,
2-(3-20 alkyl)oxyphenyl)-5-substituted pyrimidine,
5-($C_{3-20}$ alkyl)carbonyloxy)-2-(4-substituted phenyl)pyrimidine,
2-($C_{3-20}$ alkyl)carbonyloxy)-5-(4-substituted phenyl)pyrimidine,
2-($C_{3-20}$ alkyl)carbonyloxyphenyl)-5-substituted pyrimidine,
5-($C_{3-20}$ alkyl)oxycarbonyl)-2-(4-substituted phenyl)pyrimidine,
2-(($C_{3-20}$ alkyl)oxycarbonylphenyl)-5-substituted pyrimidine.

In the above designation of compounds, "substituted" refers to substitution with a substituent such as mentioned below:
2-alkyl($R^2$)oxy-1-propyl, 3-alkyl($R^2$)oxy-1-butyl,
4-alkyl($R^2$)oxy-1-pentyl, 5-alkyl($R^2$)oxy-1-hexyl,
6-alkyl($R^2$)oxy-1-heptyl, 7-alkyl(R2)oxy-1-octyl,
8-alkyl($R^2$)oxy-1-nonyl, 9-alkyl($R^2$)oxy-1-decyl,
10-alkyl($R^2$)oxy-1-undecyl, 11-alkyl($R^2$)oxy-1-dodecyl,
3-alkyl($R^2$)oxy-1-butenyl, 4-alkyl($R^2$)oxy-1-pentenyl,
5-alkyl($R^2$)oxy-1-hexenyl, 6-alkyl($R^2$)oxy-1-heptenyl,
7-alkyl($R^2$)oxy-1-octenyl, 8-alkyl($R^2$)oxy-1-nonenyl,
9-alkyl($R^2$)oxy-1-decenyl, 10-alkyl($R^2$)oxy-1-undecenyl,
11-alkyl($R^2$)oxy-1-dodecenyl,
3-alkyl($R^2$)oxy-1-propyl, 4-alkyl($R^2$)oxy-1-butyl,
5-alkyl($R^2$)oxy-1-pentyl, 6-alkyl($R^2$)oxy-1-hexyl,
7-alkyl($R^2$)oxy-1-heptyl, 8-alkyl($R^2$)oxy-1-octyl,
9-alkyl($R^2$)oxy-1-nonyl, 10-alkyl$OR^2$)oxy-1-decyl,
3-alkyl($R^2$)oxy-1-propenyl, 4-alkyl($R^2$)oxy-1-butenyl,
5-alkyl($R^2$)oxy-1-pentenyl, 6-alkyl($R^2$)oxy-1-hexenyl,
7-alkyl($R^2$)oxy-1-heptenyl, 8-alkyl($R^2$)oxy-1-octenyl,
8-alkyl($R^2$)oxy-1-nonenyl, 10-alkyl($R^2$)oxy-1-decenyl,
2-alkyl($R^2$)oxy-3,3,3-trifluoro-1-propyl,
3-alkyl($R^2$)oxy-4,4,4-trifluoro-1-butyl,
1-alkyl($R^2$)oxy-2,2,2-trifluoro-ethyl,
4-alkyl($R^2$)oxy-5,5,5-trifluoro-1-pentyl,
5-alkyl($R^2$)oxy-6,6,6-trifluoro-1-hexyl,
6-alkyl($R^2$)oxy-7,7,7-trifluoro-1-heptyl,
7-alkyl($R^2$)oxy-8,8,8-trifluoro-1-octyl,
8-alkyl($R^2$)oxy-9,9,9-trifluoro-1-nonyl,
9-alkyl($R^2$)oxy-10,10,10-trifluoro-1-decyl,
10-alkyl($R^2$)oxy-11,11,11-trifluoro-1-undecyl,
11-alkyl($R^2$)oxy-12,12,12-trifluoro-1-dodecyl,
3-alkyl($R^2$)oxy-4,4,4-trifluoro-1-butenyl,
4-alkyl($R^2$)oxy-5,5,5-trifluoro-1-pentenyl,
5-alkyl($R^2$)oxy-6,6,6-trifluoro-1-hexenyl,
6-alkyl($R^2$)oxy-7,7,7-trifluoro-1-heptenyl,
7-alkyl($R^2$)oxy-8,8,8-trifluoro-1-octenyl,
8-alkyl($R^2$)oxy-9,9,9-trifluoro-1-nonenyl,
9-alkyl($R^2$)oxy-10,10,10-trifluoro-1-decenyl,
10-alkyl($R^2$)oxy-11,11,11-trifluoro-1-undecenyl,
11-alkyl($R^2$)oxy-12,112,12-trifluoro-1,dodecenyl (in the above-shown substituents, "alkyl($R^2$)" refers to an alkyl group with 1–20 carbon atoms or an alkoxyalkyl group with 2–20 carbon atoms which may be substituted with a halogen atom),
2-alkyl($R^2$)carbonyloxy-1-propyl, 3-alkyl($R^2$)-carbonyloxy-1-butyl, 4-alkyl($R^2$)carbonyloxy-1-pentyl,
5-alkyl(R2)carbonyloxy-1-hexyl, 6-alkyl($R^2$)-carbonyloxy-1-heptyl, 7-alkyl(R2)carbonyloxy-1-octyl,
8-alkyl($R^2$)carbonyloxy-1-nonyl, 9-alkyl($R^2$)-carbonyloxy-1-decyl, 10-alkyl(R2)carbonyloxy-1-undecyl,
11-alkyl($R^2$)carbonyloxy-1-dodecyl, 3-alkyl ($R^2$)-carbonyloxy- 1-butenyl, 4-alkyl($\$^2$)carbonyloxy-1pentenyl,
5-alkyl($R^2$)carbonyloxy-1-hexenyl, 6-alkyl($R^2$)carbonyloxy-1-heptenyl, 7-alkyl($R^2$)-carbonyloxy- 1-octenyl, 8-alkyl($R^2$)carbonyloxy-1-nonenyl, 9-alkyl($R^2$)carbonyloxy-1-decenyl,
10-alkyl($R^2$)carbonyloxy-1-undecenyl, 11-alkyl($R^2$)-carbonyloxy- 1-dodecenyl, 3-alkyl($R^2$)carbonyloxy-1-propyl, 4-alkyl($R^2$)carbonyloxy-1-butyl,
5-alkyl($R^2$)carbonyloxy-1-pentyl, 6-alkyl($R^2$)-carbonyloxy-1-hexyl, 7-alkyl($R^2$)carbonyloxy-1-heptyl,
8-alkyl($R^2$)carbonyloxy-1-octyl, 9-alkyl($R^2$)-carbonyloxy-1-nonyl, 10-alkyl(R2)carbonyloxy-1-decyl,
3-alkyl($R^2$)carbonyloxy-1-propenyl, 4-alkyl($R^2$)-carbonyloxy- 1-butenyl, 5-alkyl($R^2$)carbonyloxy-1-pentenyl, 6-alkyl($R^2$)carbonyloxy-1-hexenyl,
7-alkyl($R^2$)carbonyloxy-1-heptenyl, 8-alkyl($R^2$)-carbonyloxy- 1-octenyl, 9-alkyl($R^2$)carbonyloxy-1-nonenyl, 10-alkyl($R^2$)carbonyloxy-1-decenyl,
2-alkyl($R^2$)carbonyloxy-3,3,3-trifluoro-1-propyl,
3-alkyl($R^2$)carbonyloxy-4,4,4-trifluoro-1-butyl,
4-alkyl($R^2$)carbonyloxy-5,5,5-trifluoro-1-pentyl,
5-alkyl($R^2$)carbonyloxy-6,6,6-trifluoro-1-hexyl,
6-alkyl($R^2$)carbonyloxy-7,7,7-trifluoro-1-heptyl,
7-alkyl($R^2$)carbonyloxy-8,8,8-trifluoro-1-octyl,
8-alkyl($R^2$)carbonyloxy-9,9,9-trifluoro-1-nonyl,
9-alkyl($R^2$)carbonyloxy-10,10,10-trifluoro-1-decyl,
10-alkyl($R^2$)carbonyloxy-11,11,11-trifluoro-1-undecyl,
11-alkyl($R^2$)carbonyloxy-12,12,12-trifluoro-1-undecyl,
3-alkyl($R^2$)carbonyloxy-4,4,4-trifluoro-1-butenyl,
4-alkyl($R^2$)carbonyloxy-5,5,5-trifluoro-1-pentenyl,
5-alkyl($R^2$)carbonyloxy-6,6,6-trifluoro-1-hexenyl,
6-alkyl($R^2$)carbonyloxy-7,7,7-trifluoro-1-heptenyl,
7-alkyl($R^2$)carbonyloxy-8,8,8-trifluoro-1-octenyl,
8-alkyl($R^2$)carbonyloxy-9,9,9-trifluoro-1-nonenyl,
9-alkyl($R^2$)carbonyloxy-10,10,10-trifluoro-1-decenyl,
10-alkyl($R^2$)carbonyloxy-11,11,11-trifluoro-1-undecenyl, and
11-alkyl($R^2$)carbonyloxy-12,12,12-trifluoro-1-dodecenyl.

The optical active alcohols represented by the formula II-a include the following:
5-alkyl-2-(1-hydroxy-2,2,2-trifluoroethyl)phenyl-pyrimidine, 5-alkoxy-2-(1-hydroxy-2,2,2-trifluoroethyl)phenylpyrimidine, 5-alkylcarbonyloxy-2-(1-hydroxy-2,2,2-trifluoroethyl)-phenylpyrimidine,
5-alkyloxycarbonyl-2-(1-hydroxy-2,2,2-trifluoro-ethyl)phenylpyrimidine, 2-alkylphenyl-5-(1-hydroxy-2,2,2-trifluoroethyl)pyrimidine, 2-alkyloxyphenyl-5-(1-hydroxy-2,2,2-trifluoroethyl)pyrimidine,
2-alkylcarbonyloxyphenyl-5-(1-hydroxy-2,2,2-trifluoroethyl)pyrimidine, 2-alkyloxycarbonylphenyl-5-(1-hydroxy-2,2,2-trifluoroethyl)pyrimidine,
2-alkyl-5-(1-hydroxy-2,2,2-trifluoroethyl)phenylpyrimidine, 2-alkyloxy-5-(1-hydroxy-2,2,2-trifluoroethyl)phenylpyrimidine,
2-alkylcarbonyloxy-5-(1-hydroxy- 2,2,2-trifluoroethyl)phenylpyrimidine, 2-alkyloxycarbonyl-5-(1-hydroxy-2,2,2-trifluoroethyl)phenylpyrimidine, and the compounds having the above structures in which the substituent (1-hydroxy-2,2,2-trifluoroethyl) group was replaced by any of 2-hydroxy-3,3,3-trifluoropropyl, 3-hydroxy-4,4,4-trifluorobutyl, 4-hydroxy-5,5,5-trifluoropentyl,
5-hydroxy-6,6,6-trifluorohexyl, 6-hydroxy-7,7,7-trifluoroheptyl, 3-hydroxy-4,4,4-trifluoro-1-butenyl,
4-hydroxy-5,5,5-trifluoro-1-pentenyl, 5-hydroxy-6,6,6-trifluoro-1-hexenyl, 6-hydroxy-7,7,7-trifluoro-1-heptenyl, 7-hydroxy-8,8,8-trifluorooctyl,
8-hydroxy-9,9,9-trifluorononyl, 9-hydroxy-10,10,10-trifluorodecyl, 10-hydroxy-11,11,11-trifluoroundecyl, 11-hydroxy-12,12,12-trifluoro-dodecyl,
7-hydroxy-8,8,8-trifluoro-1-octenyl, 8-hydroxy-9,9,9-trifluoro- 1-nonenyl, 9-hydroxy-10,10,10-trifluoro-1-decenyl, 10-hydroxy-11,11,11-trifluoro-1-undecyl,
and 11-hydroxy-12,12,12-trifluoro-1-dodecenyl. In the above designation of compounds, "alkyl" refers to an alkyl group having 3 to 20 carbon atoms. The optical active alcohols of the formula II-a also include the following:
5-alkyl-2-(1-hydroxyethyl)phenylpyrimidine,
5-alkyloxy-2-(1-hydroxyethyl)phenylpyrimidine,
5-alkylcarbonyloxy-2-(1-hydroxyethyl)phenylpyrimidine,
5-alkyloxycarbonyl-2-(1-hydroxyethyl)phenylpyrimidine,
2-alkylphenyl-5-(1-hydroxyethyl)pyrimidine,
2-alkyloxyphenyl-5-(1-hydroxyethyl)-pyrimidine,
2-alkylcarbonyloxyphenyl-5-(1-hydroxyethyl)pyrimidine,
2-alkyloxycarbonylphenyl-5-(1-hydroxyethyl)pyrimidine,
2-alkyl-5-(1-hydroxyethyl)phenylpyrimidine,
2-alkyloxy-5-(1-hydroxyethyl)phenylpyrimidine,
2-alkylcarbonyloxy-5-(1-hydroxyethyl)phenylpyrimidine,
2-alkoxycarbonyl-5-(1-hydroxyethyl)phenylpyrimidine,
and the compounds having the above structures in which the substituent (1-hydroxyethyl) group was replaced by any of 2-hydroxypropyl, 3-hydroxybutyl,
4-hydroxypentyl, 5-hydroxyhexyl, 6-hydroxyheptyl,
3-hydroxy-1-butenyl, 4-hydroxy-1-pentenyl,
5-hydroxy-1-hexenyl, 6-hydroxy-1-heptenyl,
7-hydroxyoctyl, 8-hydroxynonyl, 9-hydroxydecyl,
10-hydroxyundecyl, 11-hydroxy-dodecyl, 7-hydroxy-1-octenyl, 8-hydroxy-1-nonenyl, 9-hydroxy-1-decenyl,
10-hydroxy-1-undecenyl and 11-hydroxy-1-dodecenyl.

In the above designation of compounds, "alkyl" refers to an alkyl group with 3–20 carbon atoms.

The liquid crystal compositions according to the present invention contain at least one of the phenylpyrimidine derivatives represented by the formula I as an essential component. The content of the compound of the formula I may range widely from 0.1 to 99.9% by weight, preferably 1 to 99% by weight, based on the produced liquid crystal composition. The liquid crystal compositions of this invention find useful application to the liquid crystal elements such as optical switching elements. In such application of said liquid crystal compositions, the conventional methods can be used with no specific restrictions.

The phenylpyrimidine derivatives of the formula 1 according to the present invention, even when not showing a liquid crystal phase in themselves, can be utilized for the liquid crystal elements by forming a liquid crystal composition with no need of increasing the viscosity.

Among the phenylpyrimidine derivatives represented by the formula I according to the present invention, those of the formula I wherein $R^1$ is an alkyl group with 5–16 carbon atoms and Y is $-(CH_2)_m-$ is especially preferred for the reason of chemical stability in use as a component of liquid crystal compositions. Also, from the viewpoint of liquid crystal properties, it is preferred that m is a number of 2 or greater.

The compounds of the formula I wherein Z is fluorine atom have better liquid crystal properties in the low temperature region and are also higher in the degree of spontaneous polarization than the compounds of the formula I wherein Z is hydrogen atom.

When p is 1 and s is also 1 in the formula I, the compounds of the formula I are excellent in action for elevating spontaneous polarization in liquid crystal compositions and conducive to enhancement of response speed.

As described above, the phenylpyrimidine derivatives represented by the formula I according to the present invention have very excellent liquid crystal properties and can be used advantageously for the preparation of liquid crystal compositions and for the production of liquid crystal elements using such compositions.

PREFERRED EMBODIMENTS

The present invention will hereinafter be described more particularly with reference to the examples thereof. It is to be understood, however, that these examples are merely intended to be illustrative and not restrictive to the scope of the invention.

Referential Example 1

78 g (0.2 mol) of 2-(4-bromophenyl)-5-decyloxy-pyrimidine, 46 g (0.3 mol) of 1,1,1-trifluoro-2-acetoxy-3-butene, 50 g of sodium bicarbonate and 150 ml of N-methylpyrrolidone were supplied into a four-necked flask equipped with a stirrer and a thermometer. Then 1.6 g of triphenylphosphine and 0.6 g of palladium acetate were added into the flask and the mixture was stirred under heating at 110°–120° C. in a nitrogen atmosphere for 20 hours.

The resulting reaction mixture was poured into 500 ml of water and extracted with 500 ml of toluene. The resultantly formed toluene layer was washed with water and then concentrated under reduced pressure, which gave a dark brown residue. This residue was purified by silica gel column chromatography using a toluene-ethyl acetate mixture as eluent to obtain 42 g of 2-(4-(3-acetoxy-4,4,4-trifluoro-1-butenyl)phenyl)-5-decyloxypyrimidine (II-b-1) in a yield of 45%.

23 g (50 mmol) of the above product II-b-1 was added into a mixture of 500 ml of 0.3M phosphate buffer (pH 7.0), 10 ml of chloroform and 3 g of Lipase P (a lipase of the genus Pseudomonas, produced by Amano Pharmaceutical Co., Ltd.) and stirred vigorously at 36°–38° C. for 30 hours.

The resulting mixture was extracted with 200 ml of toluene, and the resultantly formed organic layer was washed with water and concentrated under reduced pressure. The residue was subjected to silica gel column chromatography using a toluene-ethyl acetate mixture as eluent to obtain 10 g of (−)-2-(4-(3-hydroxy-4,4,4-trifluoro-1-butenyl)phenyl)-5-decyloxypyrimidine (II-a-1) (yield: 48% $[\alpha]_D^{20}=-15.1°$ (c=1, chloroform)) and 11.8 g of (−)-2-(4-(3-acetoxy-4,4,4-trifluoro-1-butenyl) phenyl)-5-decyloxypyrimidine (yield: 50%; $[\alpha]_D^{20}=-4.5°$ (c=1, chloroform)).

4.2 g (10 mmol) of the above product II-a-1 was dissolved in 20 ml of tetrahydrofuran, and the solution was added with 0.05 g of 10% Pd/C and subjected to a hydrogenation reaction in a hydrogen atmosphere under normal pressure. The reaction was stopped at the time when about 230 ml of hydrogen was consumed. Then 10% Pd/C was filtered out and the filtrate was concentrated to give 4.2 g of (−)-2-(4-(3-hydroxy-4,4,4-trifluorobutyl)phenyl)-5-decyloxypyrimidine. Yield: 100%; $[\alpha]_D^{20}=-14.9°$ (c=1, chloroform).

Referential Examples 2–5

The procedure of Referential Example 1 was followed except that 2-(4-bromophenyl)-5-decyloxypyrimidine and 1,1,1-trifluoro-2-acetoxy-3-butene used in Referential Example 1 were replaced by the compounds shown in Table 1. The results are shown in Table 1.

TABLE 1

| Referential Example No. | Halide | (Amount used) | Olefin | (Amount used) | Compound (II-a')*[1] Yield | Compound (II-a')*[1] $[\alpha]_D^{20}$ (c = 1, CHCl₃) | Compound (II-a)*[2] Yield | Compound (II-a)*[2] $[\alpha]_D^{20}$ (c = 1, CHCl₃) |
|---|---|---|---|---|---|---|---|---|
| 2 | 2-(4-bromophenyl)-5-decyloxy-pyrimidine | (7.8 g) | CH₂=CH–CH(OAc)–CF₃ | (6.6 g) | 81% × 48% | −13.2° | 99% | −13.1° |
| 3 | 2-(4-bromophenyl)-5-decyloxy-pyrimidine | (7.8 g) | CH₂=CH–CH₂–CH(OAc)–CF₃ | (5.4 g) | 80% × 47% | −11.5° | 100% | −11.6° |
| 4 | 2-(4-decyloxyphenyl)-5-bromo-pyrimidine | (7.8 g) | CH₂=CH–CH₂–CH(OAc)–CF₃ | (5.4 g) | 88% × 48% | −12.0° | 100% | −11.8° |
| 5 | 2-(4-bromophenyl)-5-decylpyrimidine | (7.5 g) | CH₂=CH–CH₂–CH(OAc)–CF₃ | (5.4 g) | 90% × 48% | −12.0° | 100% | −12.0° |

(II-a')*[1]:

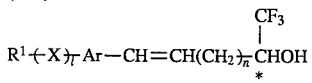

(II-a)*[1]:

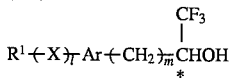

Referential Example 6

7.8 g (0.02 mol) of 2-(4-bromophenyl)-5-decyloxypyrimidine, 3.4 g (0.03 mol) of 2-acetoxy-3-butene, 5 g of sodium bicarbonate and 10 ml of N-methylpyrrolidone were supplied into a four-necked flask provided with a stirrer and a thermometer. The mixture in the flask was further added with 0.16 g of triphenylphosphine and 0.06 g of palladium acetate and stirred under heating at 110°–120° C. in a nitrogen atmosphere for 20 hours.

The reaction mixture was poured into 200 ml of water and extracted with 200 ml of toluene. The resultantly formed toluene layer was washed with water and concentrated under reduced pressure to obtain a dark brown residue. This residue was purified by silica gel column chromatography using toluene/ethyl acetate as eluent to obtain 3.6 g of 2-(4-(3-acetoxy-1-butenyl)phenyl)-5-decyloxypyrimidine (II-b-6). Yield: 42%.

2.1 g (5 mmol) of the above product II-b-6 was added into a mixture of 50 ml of 0.3M phosphate buffer (pH 7.0), 5 ml of chloroform and 0.5 g of Lipase P (a lipase of the genus Pseudomonas, produced by Amano Pharmaceutical Co., Ltd.) and the whole mixture was stirred vigorously at 36°–38° C. for 30 hours.

The resulting mixture was extracted with 200 ml of toluene, and the organic layer was washed with water and concentrated under reduced pressure. The residue was subjected to silica gel column chromatography (eluent: toluene/ethyl acetate) to obtain 0.94 g of (−)-2-(4-(3-hydroxy-1-butenyl)phenyl)-5-decyloxypyrimidine (II-a-6) (yield: 49%; $[\alpha]_D^{20}=-8.5°$ (c=1, chloroform) and 1.06 g of (−)-2-(4-(3-acetoxy-1-butenyl)phenyl-5-decyloxy pyrimidine (yield: 50%; $[\alpha]_D^{20}=-10.1°$ (c=1, chloroform).

0.39 g (1 mmol) of the above product II-a-6 was dissolved in 20 ml of tetrahydrofuran, and the solution was added with 10% Pd/C and subjected to a hydrogenation reaction in a hydrogen atmosphere under normal pressure. The reaction was stopped at the instant when about 25 ml of hydrogen was consumed. Then 10% Pd/C was filtered out and the filtrate was concentrated to obtain 0.38 g of (−)-2-(4-(3-hydroxybutyl)phenyl)-5-decyloxypyrimidine. Yield: 100%; $[\alpha]_D^{20}=-5.5°$ (c=1, chloroform).

Referential Example 7

7.8 g (0.02 mol) of 2-(4-bromophenyl)-5-decyloxypyrimidine, 2.9 g (0.04 mol) of 3-butene-1-ol, 5 g of sodium bicarbonate and 10 ml of N-methylpyrrolidone were supplied into a four-necked flask furnished with a stirrer and a thermometer. Then 0.16 g of triphenylphosphine and 0.06 g of palladium acetate were added into the flask and the mixture was stirred under heating at 110°–120° C. in a nitrogen atmosphere for 2 hours.

The resulting reaction mixture was poured into 200 ml of water and extracted with toluene. The toluene layer so formed was washed with water and concentrated under reduced pressure to obtain a dark brown residue. The residue was purified by subjecting it to silica gel column chromatography using toluene/ethyl acetate as eluent to give 6.2 g of 2-(4-(4-hydroxy-1-butenyl)phenyl)-5-decyloxypyrimidine (yield: 81%).

0.38 g (1 mmol) of the thus obtained 2-(4-(4-hydroxy-1-butenyl)phenyl)-5-decyloxypyrimidine was dissolved in 20 ml of tetrahydrofuran, added with 0.05 g of 10% Pd/C and subjected to a hydrogenation reaction in a hydrogen atmosphere under normal pressure. The reaction was stopped when about 25 ml of hydrogen was consumed. Then 10% Pd/C was filtered out and the filtrate was concentrated to obtain 0.38 g of 2-(4-(4-hydroxybutyl)-phenyl)- 5-decyloxypyrimidine (yield: 99%).

Referential Examples 8–10

The procedure of Referential Example 7 was followed except that the compounds shown in Table 2 were used in place of 2-(4-bromophenyl)-5-decyloxypyrimidine and 3-butene-1-ol used in Referential Example 7. The results are shown in Table 2 which also shows the results of Referential Example 7.

TABLE 2

| Referential Example No. | Halide | (Amount used) | Olefin | (Amount used) | Compound (II-d) (R''' = H) Yield | properties | Compound (II-e) (R'' = H) Yield | Properties |
|---|---|---|---|---|---|---|---|---|
| 7 | 2-(4-bromophenyl)-5-decyloxy-pyrimidine | (7.8 g) | 3-butene-1-ol | (2.9 g) | 81% | M.p. 10–15° C. | 99% | Colorless oil at room temp. |
| 8 | 2-(4-bromophenyl)-5-decyloxy-pyrimidine | (7.8 g) | 4-pentene-1-ol | (3.4 g) | 84% | M.p. 15–21° C. | 100% | Colorless oil at room temp. |
| 9 | 2-(4-decyloxy-phenyl)-5-bromo-pyrimidine | (7.8 g) | 4-pentene-1-ol | (3.4 g) | 85% | M.p. 10–16° C. | 100% | Colorless oil at room temp. |
| 10 | 2-(4-bromophenyl)-5-decylpyrimidine | (7.5 g) | 5-hexene-1-ol | (4.0 g) | 90% | Colorless oil at room temp. | 100% | Colorless oil at room temp. |

Referential Example 11

35.5 g (0.1 mol) of 2-(4-acetylphenyl)-5-decyloxypyrimidine, 300 ml of ethanol and 300 ml of chloroform were supplied into a four-necked flask equipped with a stirrer and a thermometer. Then 2.8 g (0.075 mol) of sodium borohydride was added at 30°–40° C. and the mixture was stirred at the same temperature for 4 hours. The resulting reaction mixture was poured into 500 ml of water, followed by extraction and liquid separation, and the obtained chloroform layer was washed with water, then dried over anhydrous magnesium sulfate and concentrated under reduced pressure to obtain 35.8 g of 2-(4-(1-hydroxyethyl)phenyl)-5-decyloxypyrimidine (II-c-11) (yield: 100%).

32 g (0.09 mol) of the above product II-c-11 was dissolved in a mixed solvent comprising 300 ml of toluene and 100 ml of pyridine, and the solution was added with 12.2 g (0.12 mol) of acetic anhydride and 1 g of 4-pyrrolidinopyridine and stirred at 30°–40° C. for 4 hours.

The reaction mixture was poured into 500 ml of water, and after liquid separation, the toluene layer was washed with 1N hydrochloric acid, water, a 5% sodium bicarbonate solution and water successively in that order, then dried over anhydrous magnesium sulfate and freed of solvent in vacuo to obtain 35.8 g of 2-(4-(1-acetoxy-ethyl)phenyl)- 5-decyloxypyrimidine (II-b-11) as a white solid (yield: 99.5%).

31.9 g (0.08 mol) of the above product II-b-11 was added into a mixture of 500 ml of 0.3M phosphate buffer (pH 7.0), 20 ml of chloroform and 3.2 g of Lipase P (a lipase of the genus Pseudomonas, produced by Amano Pharmaceutical Co., Ltd.) and stirred vigorously at 36°–38° C. for 20 hours.

The resulting mixture was extracted with 400 ml of methyl isobutylketone, and the organic layer was washed with water and concentrated under reduced pressure. The obtained residue was subjected to silica gel column chromatography using toluene/chloroform/ethyl acetate mixture as eluent to yield 14.0 g of (+)-2-(4-(1-hydroxy-ethyl)phenyl)- 5-decyloxypyrimidine (II-a-11) (yield: 49%; $[\alpha]_D^{20}=+26.0°$ (c=1, chloroform); m p. 65°–66° C.) and 16.1 g of (−)-2-(4-(1-acetoxyethyl)phenyl)-5-decyloxy-pyrimidine (yield: 50%; $[\alpha]_D^{20}=-71.5°$ (c=1, chloroform; m.p. 42°–43° C.).

4 g of the above product (−)-(4-(1-acetoxy-ethyl)phenyl)-5-decyloxypyrimidine was dissolved in a mixture of 50 ml of methanol and 10 ml of a 20% sodium hydroxide solution, stirred at 30° C. for 2 hours and hydrolyzed, and the resulting reaction solution was extracted by adding 200 ml of water and 200 ml of toluene, followed by liquid separation. The obtained organic layer was dried over anhydrous magnesium sulfate and cleared of solvent in vacuo to yield 3.5 g of (−)-(4-(1-hydroxy-ethyl)phenyl)- 5-decyloxypyrimidine as a white solid.

Referential Example 12

The procedure of Referential Example 11 was followed except for use of 38.3 g (0.1 mol) of 2-(4-acetylphenyl)-5-decylcarbonyloxypyrimidine in place of 35.5 g of 2-(4-acetylphenyl)-5-decyloxypyrimidine, forming an asymmetric hydrolyzate by use of an enzyme to obtain 13 g of (+)-2-(4-(1-hydroxyethyl)phenyl)-5-decylcarbonyloxypyrimidine (II-a-12), $[\alpha]_D^{20}=+24.5°$ (c=1, chloroform).

Referential Example 13

The procedure of Referential Example 11 was followed except for use of 32.6 g (0.1 mol) of 2-(4-acetylphenyl)-5-octyloxypyrimidine in place of 35.5 g of 2-(4-acetylphenyl)-5-decyloxypyrimidine, forming an asymmetric hydrolyzate by use of an enzyme to obtain 12.5 g of (+)-2-(4-(1-hydroxyethyl)phenyl-5-octyloxypyrimidine (II-a-13).

$[\alpha]_D^{20}=+26.9°$ (c=1, chloroform)

Referential Example 14

7.3 g (0.02 mol) of 2-(4-bromophenyl)-5-octyloxypyrimidine, 3.4 g (0.03 mol) of 2-acetoxy-3-butene, 5 g of tri-n-butylamine and 10 ml of N-methyl-pyrrolidone were supplied into a four-necked flask equipped with a stirrer and a thermometer, followed by addition of 0.16 g of triphenylphosphine and 0.06 g of palladium acetate and 25-hour stirring under heating at 120° C. in a nitrogen atmosphere.

The reaction mixture was poured into 200 ml of water and extracted with 200 ml of toluene. The resultantly formed toluene layer was washed with water and concentrated under reduced pressure to obtain a dark brown residue. This residue was purified by silica gel column chromatography (eluent: toluene/ethyl acetate) to obtain 4.0 g of 2-(4-(3-acetoxy-1-butenyl)phenyl)-5-octyloxypyrimidine (II-c-'14). Yield: 51%.

3.96 g (10 mmol) of the above product II-c'-14 was dissolved in 30 ml of tetrahydrofuran, then added with 0.5 g of 5% Pd/C and subjected to a hydrogenation reaction in a hydrogen atmosphere. The reaction was stopped when about 230 ml of hydrogen was consumed. Then 10% Pd/C was filtered out and the filtrate was concentrated to obtain 3.97 g of 2-(4-(3-acetoxybutyl)phenyl)-5-octyloxypyrimidine (II-c''-14). Yield: 100%.

2.0 g (5 mmol) of the above product II-c''-14 was added into a mixture of 50 ml of 0.3M phosphate buffer (pH 7.0), 5 ml of chloroform and 0.5 g of a lipase of the genus Arthrobacter and stirred vigorously at 36°–38° C. for 30 hours.

The resulting mixture was extracted with 200 ml of toluene, and the organic layer was washed with water and concentrated under reduced pressure. The residue was subjected to silica gel column chromatography (eluent: toluene/ethyl acetate) to obtain 0.86 g of (−)-2-(4-(3-hydroxybutyl)phenyl)- 5-octyloxypyrimidine (II-a-14) (yield: 48%; $[\alpha]_D^{20}=-5.6°$ (c=1, chloroform) and 1.01 g of (−)-2-(4-(3-acetoxybutyl)phenyl)-5-octyloxypyrimidine (yield: 50%; $[\alpha]_D^{20}=-5.2°$ (c=1, chloroform)

Referential Examples 15–30

The procedure of Referential Example 1 was followed except for use of the starting materials shown in Table 3 to obtain the corresponding optically active unsaturated alcohols (II-a') and optically active alcohols (II-a) shown in Table 3.

TABLE 3

| Example No. | Halide (V) | Olefin (VI) | R | 1 | X |
|---|---|---|---|---|---|
| 15 |  C$_{10}$H$_{21}$O–[pyrimidine]–[phenyl]–I | CH$_2$=CHCH$_2$CHOAc (CH$_3$) | C$_{10}$H$_{21}$ | 1 | O |
| 16 | 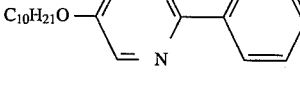 C$_{16}$H$_{33}$O–[pyrimidine]–[phenyl]–Br | " | C$_{16}$H$_{33}$ | 1 | O |

TABLE 3-continued
| | | | | | | |
|---|---|---|---|---|---|---|
| 17 | 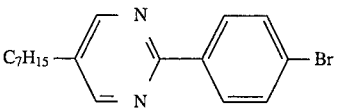 | " | | C₇H₁₅ | 0 | — |
| 18 | 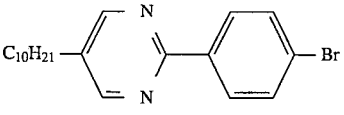 | " | | C₁₀H₂₁ | 0 | — |
| 19 | 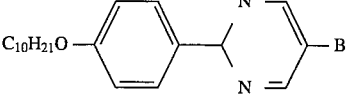 | " | | C₁₀H₂₁ | 1 | O |
| 20 | 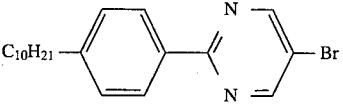 | CH₂=CHCH₂C̱HOAc (CH₃) | | C₁₀H₂₁ | 0 | — |
| 21 | 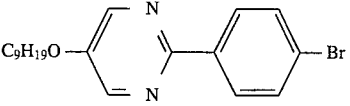 | CH₂=CH(CH₂)₂C̱HOAc (CH₃) | | C₉H₁₉ | 1 | O |
| 22 | 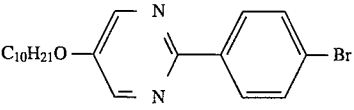 | " | | C₁₀H₂₁ | 1 | O |
| 23 | 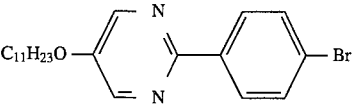 | " | | C₁₁H₂₃ | 1 | O |
| 24 | 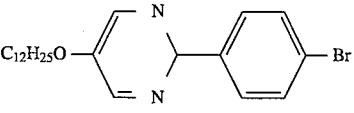 | " | | C₁₂H₂₅ | 1 | O |
| 25 | 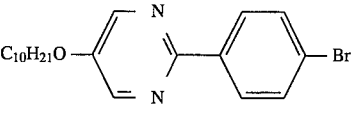 | CH₂=CH(CH₂)₃C̱HOAc (CH₃) | | C₁₀H₂₁ | 1 | O |
| 26 | 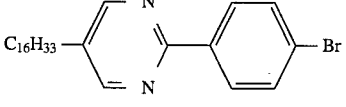 | " | | C₁₂H₂₅ | 1 | O |
| 27 | 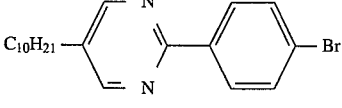 | " | | C₁₀H₂₁ | 0 | — |
| 28 | 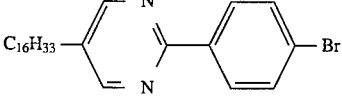 | " | | C₁₆H₃₃ | 0 | — |
| 29 | 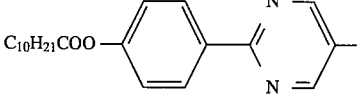 | CH₂=CH(CH₂)₂C̱HOAc (CH₃) | | C₁₀H₂₁ | 1 | —COO— |

TABLE 3-continued

| Ar | n | R'' | Unsaturated ester (II-c') Yield (%) | Optically active saturated alcohol (II-a')*1 Yield of asymmetric hydrolysis | [α]$_D^{20}$ (c = 1, CHCl$_3$) | Optically active alcohol-(II-a)*2 [α]$_D^{20}$ (c = 1, CHCl$_3$) | M.p. | Ex. No. |
|---|---|---|---|---|---|---|---|---|
| 30: C$_{10}$H$_{21}$COO—〈phenyl〉—〈pyrimidine〉—Br, CH$_2$=CH(CH$_2$)$_3$CHOAc(CH$_3$), C$_{10}$H$_{21}$, 1, —COO— | | | | | | | | |
| 〈pyrimidine-phenyl〉 | 3 | COCH$_3$ | 51 | 49 | −3.2° | −3.2° | 50–56° C. | 15 |
| " | " | " | 46 | 48 | −3.0° | −3.0° | | 16 |
| " | " | " | 40 | 48 | −3.1° | −3.4° | | 17 |
| " | " | " | 55 | 47 | −3.4° | −3.3° | | 18 |
| 〈phenyl-pyrimidine〉 | " | " | 51 | 49 | −3.5° | −3.3° | | 19 |
| 〈phenyl-pyrimidine〉 | 3 | COCH$_3$ | 52 | 47 | −3.5° | −3.0° | | 20 |
| 〈pyrimidine-phenyl〉 | 4 | " | 70 | 44 | −2.5° | −2.4° | | 21 |
| " | " | " | 71 | 48 | −2.1° | −2° | | 22 |
| " | " | " | 80 | 47 | −2.6° | −2.5° | | 23 |
| " | " | " | 78 | 48 | −2.5° | −2.5° | | 24 |
| 〈pyrimidine-phenyl〉 | 5 | COCH$_3$ | 80 | 48 | −2.0° | −2° | | 25 |
| " | " | " | 76 | 48 | −2.0° | −2° | | 26 |
| " | " | " | 75 | 45 | −2.1° | −2° | | 27 |
| " | " | " | 79 | 46 | −1.7° | −1.7° | | 28 |
| 〈phenyl-pyrimidine〉 | 4 | " | 65 | 43 | −1.7° | −1.7° | | 29 |
| 〈phenyl-pyrimidine〉 | 5 | COCH$_3$ | 70 | 44 | −1.5° | −1.8° | | 30 |

(Notes)
*2(II-a):

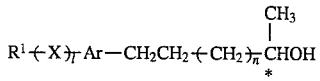

*1(II-a'):

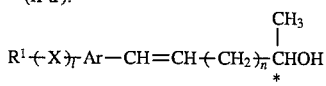

Example 1

1.0 g of (−)-2-(4-(3-hydroxy-4,4,4-trifluoro-1-butenyl)phenyl)- 5-decyloxypyrimidine was dissolved in 5 ml of butyl iodide. The solution was added with 3 g of silver oxide and stirred at 25°–30° C. for 4 days. The reaction mixture was cleared of silver oxide by filtration and concentrated under reduced pressure, and the residue was purified by silica gel column chromatography using toluene/ethyl acetate as eluent to obtain 0.98 g of (−)-2-(4-(3-butoxy-4, 4,4-trifluoro-1-butenyl)phenyl)-5-decyloxypyrimidine.

0.5 g of thus obtained (−)-2-(4-(3-butoxy4,4,4-trifluoro-1-butenyl)phenyl-5-decyloxypyrimidine was dissolved in 20 ml of tetrahydrofuran, added with 10% Pd/C and subjected to a hydrogenation reaction in a hydrogen atmosphere under normal pressure. The reaction was stopped when about 25 ml of hydrogen was consumed. Then 10% Pd/C was filtered out and the filtrate was concentrated. The resulting residue was purified by silica gel column chromatography using toluene/ethyl acetate as eluent to obtain 0.45 g of (−)-2-(4-(3-butoxy-4,4,4-trifluoro- 1-butyl)phenyl)-5-decyloxypyrimidine.

Example 2

1.0 g of (−)-2-(4-(3-hydroxy-4,4,4-trifluoro-1-butenyl)phenyl)-5-decyloxypyrimidine was dissolved in 20 ml of pyridine. The solution was added with 0.5 g of butyryl chloride and stirred at 25°–30° C. for 4 hours. The reaction mixture was diluted with 100 ml of toluene and washed with 4N hydrochloric acid, water, a 5% sodium bicarbonate solution and water successively in that order, and then the toluene layer was concentrated under reduced pressure. The residue was purified by subjecting it to silica gel column chromatography using toluene/ethyl acetate as eluent to obtain 1.08 g of (+)-2-(4-(3-butyryloxy- 4,4,4-trifluoro-1-butenyl)phenyl)-5-decyloxypyrimidine.

0.5 g of the above product was dissolved in 20 ml of tetrahydrofuran, added with 10% Pd/C and hydrogenated in a hydrogen atmosphere under normal pressure. The reaction was stopped when about 25 ml of hydrogen was consumed. Then 10% Pd/C was filtered out and the filtrate was concentrated. The residue was purified by silica gel column chromatography using toluene/ethyl acetate as eluent to detain 0.49 g of (+)-2-(4-(3-butyryloxy- 4,4,4-trifluorolbutyryl)phenyl)-5-decyloxypyrimidine.

Example 3

1.1 g (2.5 mmol) of (−)-2-(4-(4-hydroxy-5,5,5-trifluoro-1-pentyl)phenyl)-5-decyloxypyrimidine was dissolved in 10 ml of tetrahydrofuran. This solution was added with 0.12 g (3 mmol) of potassium hydride, stirred at 10°–20° C. for 20 minutes, further added with 0.85 g (3 mmol) of octyl p-toluenesulfonate and reacted at 20°–30° C. for 2 hours. The reaction mixture was poured into 100 ml of water and 100 ml of toluene, and the toluene layer was washed with water and concentrated under reduced pressure. The residue was purified by silica gel column chromatography using toluene/ethyl acetate as eluent to obtain 0.80 g of (−)-2-(4-(4-octyloxy-5,5,5-trifluoro-1-pentyl)phenyl)-5-decyloxypyrimidine.

Example 4

1.1 g (2.5 mmol) of (−)-2-(4-(4-hydroxy-5,5,5-trifluoro-1-pentyl)phenyl)-5-decyloxypyrimidine was dissolved in 10 ml of pyridine, followed by addition of 0.53 g (3 mmol) of nonanoyl chloride and 2-hour reaction at 20°–30° C. The reaction mixture was diluted with 100 ml of toluene, and the toluene layer was washed with 4N hydrochloric acid, water, a 5% sodium bicarbonate solution and water successively in that order and concentrated under reduced pressure. The residue was purified by silica gel column chromatography using toluene/ethyl acetate as eluent to obtain 1.25 g of (+)-2-(4-(4-nonanoyloxy- 5,5,5-trifluoro-1-pentyl)phenyl-5-decyloxypyrimidine.

The results of determination on the compounds obtained in Examples 1 to 4 are shown in Table 4.

Examples 5–34

The procedure of either of Examples 1 to 4 was followed except for use of the starting materials shown in Table 4 to obtain the results shown in Table 4.

TABLE 4

| Example No. | \multicolumn{5}{c}{Starting alcohol (II)} | | Carboxylic acid (III) or alkylating agent (IV) | Phenyl pyrimidine derivative (I) |
|---|---|---|---|---|---|---|---|---|
| | $R^1$ | l | X | Ar | Y | p | | S |
| 1 | n-$C_{10}H_{21}$ | 1 | O | pyrimidine-phenyl | −CH=CH− | 1 | $C_4H_9I$ | 0 |
| 2 | " | 1 | O | " | " | 1 | $C_3H_7COCl$ | 1 |
| 3 | " | 1 | O | " | −(CH$_2$)$_3$− | 1 | $C_8H_{17}OSO_2$−phenyl | 0 |
| 4 | " | 1 | O | " | " | 1 | $C_8H_{17}COCl$ | 1 |
| 5 | " | 1 | O | " | −CH=CHCH$_2$− | 1 | $C_3H_7I$ | 0 |

TABLE 4-continued

| | | | | | | | |
|---|---|---|---|---|---|---|---|
| 6 | n-C$_{10}$H$_{21}$ | 1 | O | 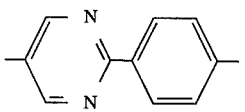 | —CH=CH(CH$_2$)$_2$— | 1 | C$_3$H$_7$I | 0 |
| 7 | " | 1 | O | " | " | 1 | C$_2$H$_5$OC$_3$H$_6$OSO$_2$— | 0 |
| 8 | " | 1 | O | " | " | 1 | CH$_3$COCl | 1 |
| 9 | " | 0 | — | " | —CH=CH—(CH$_2$)$_4$— | 1 | C$_4$H$_9$I | 0 |
| 10 | " | 1 | O | " | " | 1 | " | 0 |
| 11 | n-C$_{10}$H$_{21}$ | 1 | O | 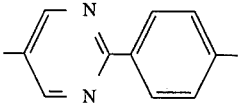 | —(CH$_2$)$_4$— | 1 | C$_5$H$_{11}$CHClCOCl, F (*) | 1 |
| 12 | " | 1 | O | " | " | 1 | C$_2$H$_5$CHCOCl, CH$_3$ (*) (S) | 1 |
| 13 | n-C$_8$H$_{17}$ | 1 | O | 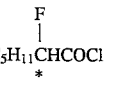 | —(CH$_2$)$_5$— | 1 | C$_3$H$_7$I | 0 |
| 14 | n-C$_{10}$H$_{21}$ | 1 | O | " | —(CH$_2$)$_3$— | 1 | " | 0 |
| 15 | " | 1 | O | 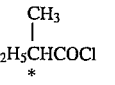 | —(CH$_2$)$_4$— | 1 | C$_4$H$_9$I | 0 |
| 16 | n-C$_{10}$H$_{21}$ | 0 | — | 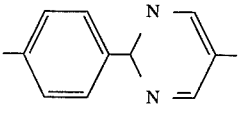 | —(CH$_2$)$_4$— | 1 | C$_4$H$_9$I | 0 |
| 17 | " | 1 | O | " | —(CH$_2$)$_6$— | 1 | C$_3$H$_7$I | 0 |
| 18 | n-C$_{16}$H$_{33}$ | 1 | O | " | —(CH$_2$)$_3$— | 1 | " | 0 |
| 19 | " | 0 | — | " | —(CH$_2$)$_5$— | 1 | " | 0 |
| 20 | " | 1 | O | " | —(CH$_2$)$_6$— | 1 | " | 0 |
| 21 | " | 1 | O | " | —(CH$_2$)$_8$— | 1 | " | 0 |
| 22 | n-C$_{10}$H$_{21}$ | 0 | — | " | —(CH$_2$)$_3$— | 1 | C$_2$H$_5$O(CH$_2$)$_4$OSO$_2$—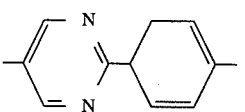 | 0 |
| 23 | " | 0 | — | " | —(CH$_2$)$_4$— | 1 | " | 0 |
| 24 | n-C$_{10}$H$_{21}$ | 0 | — | 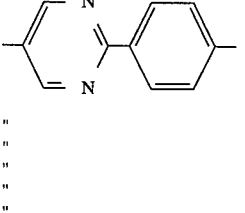 | —(CH$_2$)$_5$— | 1 | CH$_3$I | 0 |
| 25 | " | 0 | — | " | —(CH$_2$)$_6$— | 1 | " | 0 |
| 26 | " | 0 | — | " | —(CH$_2$)$_8$— | 1 | " | 0 |
| 27 | " | 1 | COO | 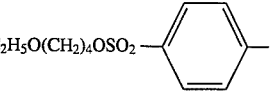 | —(CH$_2$)$_4$— | 1 | C$_3$H$_7$I | 0 |
| 28 | n-C$_7$H$_{15}$ | 0 | — | 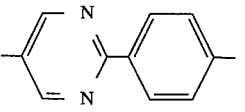 | —(CH$_2$)$_3$— | 1 | C$_8$H$_{17}$I | 0 |

TABLE 4-continued

| | | | | | | | | | | |
|---|---|---|---|---|---|---|---|---|---|---|
| 29 | n-$C_{10}H_{21}$ | 1 | O | " | —$(CH_2)_5$— | 1 | $C_3H_7I$ | | 0 | |

| | Phenylpyrimidine derivative (I) | | Hydrogenation product of phenylpyrimidine derivative (I) | | | | | |
|---|---|---|---|---|---|---|---|---|
| $R^2$ | Properties Phase transition temp. or $[\alpha]_D^{20}$ ($CHCl_3$, c = 1) | Y | P | S | $R^2$ | Properties Phase transition temp. or $[\alpha]_D^{20}$ ($CHCl_3$, c = 1) | Example followed | Ex. No. |
| $C_4H_9$ | | —$CH_2CH_2$— | 1 | 0 | $C_4H_9$ | −6.1° | — | 1 |
| $C_3H_7$ | | " | 1 | 1 | $C_3H_7$ | +2.1° | — | 2 |
| $C_8H_{17}$ | −6.2° | — | — | — | — | — | — | 3 |
| " | +0.8° | — | — | — | — | — | — | 4 |
| $C_3H_7$ | | —$(CH_2)_3$— | 1 | 0 | $C_3H_7$ | $K \underset{\leq 13}{\overline{\phantom{xx}}} Sc^* \underset{\leq 15}{\overline{\phantom{xx}}} S_A \underset{\leq 38}{\overline{\phantom{xx}48\phantom{xx}}} I$ | Example 1 | 5 |
| $C_3H_7$ | $K \xrightarrow{21} Sc^* \xrightarrow{40} S_A \xrightarrow{59} I$ | —$(CH_2)_4$— | 1 | 0 | $C_3H_7$ | $K \underset{\leq 12}{\overline{\phantom{xx}}} Sc^* \underset{\leq 26}{\overline{\phantom{xx}}} S_A \underset{\leq 40}{\overline{\phantom{xx}40\phantom{xx}}} I$ | Example 1 | 6 |
| —$(CH_2)_3OC_2H_5$ | | " | 1 | 0 | $O(CH_2)_3OC_2H_5$ | $K \xrightarrow{-40} I$ | Example 1 | 7 |
| $CH_3$ | | " | 1 | 1 | $CH_3$ | $K \xrightarrow{39} S_A \xrightarrow{51} I$ with $Sc^*$ 18, 40 | Example 2 | 8 |
| $C_4H_9$ | | —$(CH_2)_6$— | 1 | 0 | $C_4H_9$ | −2.1° | Example 1 | 9 |
| " | | " | 1 | 0 | " | −2.8° | Example 1 | 10 |
| F<br>\|<br>—$CHC_5H_{11}$<br>* | −1.1° | — | — | — | — | — | Example 4 | 11 |
| $CH_3$<br>\|<br>—$CHC_2H_5$<br>*<br>(S) | −1.8° | — | — | — | — | — | Example 4 | 12 |
| $C_3H_7$ | −3.1° | — | — | — | — | — | Example 3 | 13 |
| " | −6.2° | — | — | — | — | — | Example 3 | 14 |
| $C_4H_9$ | −6.2° | — | — | — | — | — | Example 1 | 15 |
| $C_4H_9$ | −6.1° | — | — | — | — | — | Example 1 | 16 |
| $C_3H_7$ | −2.2° | — | — | — | — | — | Example 1 | 17 |
| " | −5.5° | — | — | — | — | — | Example 1 | 18 |
| " | −3.8° | — | — | — | — | — | Example 1 | 19 |
| " | −2.2° | — | — | — | — | — | Example 1 | 20 |
| " | −1.5° | — | — | — | — | — | Example 1 | 21 |
| —$(CH_2)_4OC_2H_5$ | −5.1° | — | — | — | — | — | Example 1 | 22 |
| " | −5.6° | — | — | — | — | — | Example 1 | 23 |
| $CH_3$ | −3.2° | — | — | — | — | — | Example 1 | 24 |
| " | −2.0° | — | — | — | — | — | Example 1 | 25 |
| " | −1.8° | — | — | — | — | — | Example 1 | 26 |
| $C_3H_7$ | −4.1° | — | — | — | — | — | Example 1 | 27 |

TABLE 4-continued

| | | | | | | |
|---|---|---|---|---|---|---|
| $C_8H_{17}$ | −5.2° | — | — — — | — | | ple 1 Example 28 |
| $C_3H_7$ | −3.2° | — | — — — | — | | ple 1 Example 29 ple 1 |

Example 30

A liquid crystal composition shown in Table 5 was prepared by using the liquid crystal compounds. Preparation was conducted by placing weighed amounts of the specified compounds in a sample bottle and mixing the compounds while heating and melting them in the bottle.

Production of liquid crystal element.

A polyimide polymer film was formed on each of the two glass substrates provided with transparent electrodes of indium oxide. The film-coated substrates were rubbed in a given direction by using a gauze, with glass fiber (5 μm in diameter) placed therebetween as spacer to keep the lines of rubbing of the two substrates parallel to each other, thereby constituting a liquid crystal cell, and said liquid crystal composition (compound) was vacuum encapsulated in said cell to form a liquid crystal element.

This liquid crystal element was combined with a polarizer and an electric field of 20 V was applied thereto, observing the change in strength of transmitted light. As a result, it was confirmed that said liquid crystal element can be used as a switching element.

TABLE 5

| Example No. | Liquid crystal composition | Actually measured value of spontaneous polarization* |
|---|---|---|
| 30 | Compound of Example 6<br>$C_{10}H_{21}O$—[pyrimidine]—[phenyl]—$(CH_2)_4CHOC_3H_7$ (with $CF_3$, *)<br>20 wt. %<br><br>$C_{10}H_{21}O$—[phenyl]—COO—[phenyl]—$O(CH_2)_3CHC_2H_5$ (with $CH_3$)<br>(known compound) 80 wt. % | 19 nc/cm² (T − Tc = −10° C.) |

*Measured according to Sawyer-Tower's method

The values of spontaneous polarization and response time achievable with the compounds of the present invention were measured. The results are shown in Table 6.

TABLE 6

| | Spontaneous polarization | | |
|---|---|---|---|
| Compound | (nC/cm²) | (Temp. at the the time of measurement) | Response time* (μs) |
| Example 6 | 19 | (11° C.) | 77 (20° C.) |
| Hydrogenated compound | 37 | (3° C.) | 40 (20° C.) |
| of Example 6 | | | |
| Example 8 (Hydrogenated compound) | 47 | (15° C.) | 90 (20° C.) |

*Calculated from full width at half maximum of polarization inversion current. The figures in the parentheses are temperature at the time of measurement.

Example 31

1.0 g of (−)-2-(4-(3-(hydroxy-1-butenyl)phenyl)-5-decyloxypyrimidine was dissolved in 5 ml of butyl iodide, added with 3 g of silver oxide and stirred at −30° C. for 4 days. Then, after filtering out silver oxide, the reaction mixture was concentrated under reduced pressure and the residue was purified by silica gel column chromatography using toluene/ethyl acetate as eluent to obtain 0.98 g of (−)-2-(4-(3-butoxy-1-butenyl)phenyl)-5-decyloxypyrimidine.

0.5 g of the above product was dissolved in 20 ml of tetrahydrofuran, added with 0.05 g of 10% Pd/C and subjected to hydrogenation in a hydrogen atmosphere under normal pressure. The reaction was stopped when about 25 ml of hydrogen was consumed. Then 10% Pd/C was filtered out, followed by concentration of the filtrate and the residue was purified by silica gel column chromatography using toluene/ethyl acetate as eluent to obtain 0.45 g of (−)-2-(4-(3-butoxy-1-butyl)phenyl)-5-decyloxypyrimidine.

Example 32

1.0 g of (−)-2-(4-(3-hydroxy-1-butenyl)phenyl)-5-decyloxypyrimidine was dissolved in 20 ml of pyridine, added with 0.5 g of butyryl chloride and stirred at 25°–30° C. for 4 hours. The reaction mixture was diluted with 100 ml of toluene and washed with 4N hydrochloric acid, water, a 5% sodium bicarbonate solution and water successively in that order. The toluene layer was concentrated under reduced pressure and the residue was purified by silica gel column chromatography using toluene/ethyl acetate as eluent to obtain 1.05 g of (+)-2-(4-(3-butyryloxy-1-butenyl)phenyl)-5-decyloxy-pyrimidine.

0.5 g of the thus obtained substance was dissolved in 20 ml of tetrahydrofuran, added with 0.05 g of 10% Pd/C and subjected to a hydrogenation reaction in a hydrogen atmosphere under normal pressure. The reaction was stopped when about 25 ml of hydrogen was consumed. Then 10% Pd/C was filtered out from the reaction mixture, the filtrate was concentrated, and the residue was purified by silica gel column chromatography using toluene/ethyl acetate as eluent to Obtain 0.47 g of (+)-2-(4-(3-(butyryloxy-1-butyl)phenyl)-5-decyloxy-pyrimidine.

Example 33

1.0 g (2.5 mmol) of (−)-2-(4-(4-hydroxy-1-phenyl)phenyl)- 5-decyloxypyrimidine was dissolved in 10 ml of tetrahydrofuran, added with 0.12 g (3 mmol) of potassium hydride, stirred at 10°–20° C. for 20 minutes, then further added with 0.85 g (3 mmol) of octyl p-toluenesulfonate and reacted at 20°–30° C. for 2 hours. The reaction mixture was poured into 100 ml of water and 100 ml of toluene, and the toluene layer was washed with water and concentrated under reduced pressure. The residue was subjected to silica gel column chromatography (eluent: toluene/ethyl acetate) for purification to obtain 0.71 g of (−)-2-(4-(4-octyloxy-1-pentyl)phenyl)-5-decyloxypyrimidine.

Example 34

1.0 g (2.5 mmol) of (−)-2-(4-(4-hydroxy-1-pentyl)phenyl)- 5-decyloxypyrimidine was dissolved in 10 ml of pyridine, and the solution was added with 0.53 g (3 mmol) of nonanoyl chloride and reacted at 20°–30° C. for 2 hours.

The reaction mixture was diluted with 100 ml of toluene, and the toluene layer was washed with 4N hydrochloric acid, water, a 5% sodium bicarbonate solution and water successively in that order and concentrated under reduced pressure. The residue was purified by silica gel column chromatography using toluene/ethyl acetate as eluent to obtain 1.25 g of (+)-2-(4-(4-nonanoyloxy-1-pentyl)phenyl)- 5-decyloxypyrimidine.

The matters relating to the compounds obtained in Examples 31 to 34 are shown collectively in Table 7.

Examples 35–67

The procedure of either of Examples 31 to 34 was followed except for use of the starting materials shown in Table 7 to obtain the results also shown in Table 7.

TABLE 7

| Example No. | Starting alcohol (II) | | | | | | Carboxylic acid (III) or alkylating agent (IV) | Phenyl pyrimidine derivative (I) |
|---|---|---|---|---|---|---|---|---|
| | $R^1$ | l | X | Ar | Y | P | | S |
| 31 | n-$C_{10}H_{21}$ | 1 | O | pyrimidine-phenyl | −CH=CH− | 1 | $C_4H_9I$ | 0 |
| 32 | " | 1 | O | " | " | 1 | $C_3H_7COCl$ | 1 |
| 33 | " | 1 | O | " | −(CH$_2$)$_3$− | 1 | $C_8H_{17}OSO_2$−phenyl | 0 |
| 34 | " | 1 | O | " | " | 1 | $C_8H_{17}COCl$ | 1 |
| 35 | " | 1 | O | " | −CH=CHCH$_2$− | 1 | $C_3H_7I$ | 0 |
| 36 | n-$C_{10}H_{21}$ | 1 | O | pyrimidine-phenyl | −CH=CH(CH$_2$)$_2$− | 1 | $C_3H_7I$ | 0 |
| 37 | " | 1 | O | " | " | 1 | $C_2H_5OC_3H_6OSO_2$−phenyl | 0 |
| 38 | " | 1 | O | " | " | 1 | $CH_3COCl$ | 1 |
| 39 | " | 0 | — | " | −CH=CH−(CH$_2$)$_4$− | 1 | $C_4H_9I$ | 0 |
| 40 | " | 1 | O | " | " | 1 | " | 0 |

TABLE 7-continued

| # | R | a | X | Ring | Y | b | R' | chiral |
|---|---|---|---|---|---|---|---|---|
| 41 | n-C$_8$H$_{17}$ | 1 | O | pyrimidine-phenyl | —CH=CH(CH$_2$)$_2$— | 0 | C$_4$H$_9$I | 0 |
| 42 | " | 1 | O | " | —CH=CH(CH$_2$)$_3$— | 0 | " | 0 |
| 43 | " | 1 | O | " | " | 0 | C$_2$H$_5$OC$_3$H$_6$OSO$_2$—C$_6$H$_4$— | 0 |
| 44 | n-C$_{10}$H$_{21}$ | 1 | O | " | —(CH$_2$)$_4$— | 1 | C$_5$H$_{11}$CHF*COCl | 1 |
| 45 | " | 1 | O | " | " | 1 | C$_2$H$_5$CH(CH$_3$)*COCl (S) | 1 |
| 46 | n-C$_{10}$H$_{21}$ | 0 | — | pyrimidine-phenyl (isomer) | —(CH$_2$)$_3$— | 1 | C$_3$H$_7$I | 0 |
| 47 | n-C$_8$H$_{17}$ | 1 | O | " | —(CH$_2$)$_5$— | 1 | C$_3$H$_7$I | 0 |
| 48 | n-C$_{10}$H$_{21}$ | 1 | O | " | —(CH$_2$)$_3$— | 1 | " | 0 |
| 49 | " | 1 | O | pyrimidine-phenyl | —CH=CH(CH$_2$)$_2$— | 0 | C$_2$H$_5$CH(CH$_3$)*CH$_2$OSO$_2$—C$_6$H$_4$— (S) | 0 |
| 50 | " | 1 | O | " | —(CH$_2$)$_4$— | 1 | C$_4$H$_9$I | 0 |
| 51 | " | 0 | — | " | " | 1 | " | 0 |
| 52 | n-C$_{10}$H$_{21}$ | 1 | O | pyrimidine-phenyl | —(CH$_2$)$_6$— | 1 | C$_3$H$_7$I | 0 |
| 53 | n-C$_{16}$H$_{33}$ | 1 | O | " | —(CH$_2$)$_3$— | 1 | " | 0 |
| 54 | n-C$_{16}$H$_{33}$ | 0 | — | " | —(CH$_2$)$_5$— | 1 | " | 0 |
| 55 | " | 1 | O | " | —(CH$_2$)$_6$— | 1 | " | 0 |
| 56 | " | 1 | O | " | —(CH$_2$)$_8$— | 1 | " | 0 |
| 57 | n-C$_{10}$H$_{21}$ | 0 | — | " | —(CH$_2$)$_3$— | 1 | C$_2$H$_5$O(CH$_2$)$_4$OSO$_2$—C$_6$H$_4$— | 0 |
| 58 | n-C$_{10}$H$_{21}$ | 0 | — | pyrimidine-phenyl | —(CH$_2$)$_4$— | 1 | C$_2$H$_5$O(CH$_2$)$_4$OSO$_5$—C$_6$H$_4$— | 0 |
| 59 | n-C$_{10}$H$_{21}$ | 0 | — | " | —(CH$_2$)$_5$— | 1 | CH$_3$I | 0 |
| 60 | n-C$_{10}$H$_{21}$ | 0 | — | " | —(CH$_2$)$_6$— | 1 | " | 0 |
| 61 | " | 0 | — | " | —(CH$_2$)$_8$— | 1 | " | 0 |
| 62 | " | 1 | COO | pyrimidine-phenyl (isomer) | —(CH$_2$)$_4$— | 1 | C$_3$H$_7$I | 0 |
| 63 | n-C$_7$H$_{15}$ | 0 | — | pyrimidine-phenyl | —(CH$_2$)$_3$— | 1 | C$_8$H$_{17}$I | 0 |

5,539,115

TABLE 7-continued

| | | | | | | | | | |
|---|---|---|---|---|---|---|---|---|---|
| 64 | n-$C_{10}H_{21}$ | 1 | O | " | —$(CH_2)_5$— | 1 | $C_3H_7I$ | | 0 |
| 65 | n-$C_{10}H_{21}$ | 1 | O | " | —$(CH_2)_2$— | 1 | $CH_3COCl$ | | 1 |
| 66 | " | 1 | O | " | —$(CH_2)_3$— | 1 | " | | 1 |
| 67 | " | 1 | O | " | —$(CH_2)_6$— | 1 | " | | 1 |

| Phenylpyrimidine derivative (I) | | Hydrogenation product of phenylpyrimidine derivative (I) | | | | | Ex- |
|---|---|---|---|---|---|---|---|
| $R^2$ | Properties Phase transition temp. or $[\alpha]_D^{20}$ (CHCl$_3$, c = 1) | Y | P | S | $R^2$ | Properties Phase transition temp. or $[\alpha]_D^{20}$ (CHCl$_3$, c = 1) | ample followed | Ex. No. |

| $R^2$ | Properties | Y | P | S | $R^2$ | Properties | Ex. followed | Ex. No. |
|---|---|---|---|---|---|---|---|---|
| $C_4H_9$ | | —$CH_2CH_2$— | 1 | 0 | $C_4H_9$ | K $\xrightarrow{11}$ $S_1$ $\xrightarrow{17}$ Sc* $\xrightarrow{38}$ I | — | 31 |
| $C_3H_7$ | | " | 1 | 1 | $C_3H_7$ | K $\xrightarrow{36}$ I, $<_4$ Sc* $<_{25}$ | — | 32 |
| $C_8H_{17}$ | −1.9° | — | — | — | — | — | — | 33 |
| " | +2.1° | — | — | — | — | — | — | 34 |
| $C_3H_7$ | $\xrightarrow{-1}$ Sc* $\xrightarrow{25}$ $S_A$ $\xrightarrow{27}$ Ch $\xrightarrow{48}$ I | —(CH$_2$)$_3$— | 1 | 0 | $C_3H_7$ | K $\xrightarrow{-7}$ $S_1$ $\xrightarrow{7}$ Sc* $\xrightarrow{34}$ I | Example 31 | 35 |
| $C_3H_7$ | $\xrightarrow{18}$ Sc* $\xrightarrow{38}$ Ch $\xrightarrow{47}$ I | —(CH$_2$)$_4$— | 1 | 0 | $C_3H_7$ | K $\xrightarrow{-3}$ $S_1$ $\xrightarrow{8}$ Sc* $\xrightarrow{47}$ I | Example 31 | 36 |
| —(CH$_2$)$_3$O$C_2H_5$ | | " | 1 | 0 | (CH$_2$)$_3$O$C_2H_5$ | $S_2$ $\xrightarrow{-19}$ $S_1$ $\xrightarrow{-2}$ Sc* $\xrightarrow{31}$ I | Example 31 | 37 |
| $CH_3$ | $\xrightarrow{2}$ Sc* $\xrightarrow{32}$ Ch $\xrightarrow{50}$ I | " | 1 | 1 | $CH_3$ | $\xrightarrow{-20}$ Sc* $\xrightarrow{20}$ $S_A$ $\xrightarrow{38}$ I | Example 32 | 38 |
| $C_4H_9$ | −1.5° | —(CH$_2$)$_6$— | 1 | 0 | $C_4H_9$ | −1.6° | Example 31 | 39 |
| " | | " | 1 | 0 | " | $S_1$ $\xrightarrow{7}$ Sc* $\xrightarrow{44}$ I | Example 31 | 40 |
| $C_4H_9$ | | —(CH$_2$)$_4$— | 0 | 0 | $C_4H_9$ | $S_1$ $\xrightarrow{10}$ Sc $\xrightarrow{30}$ $S_A$ $\xrightarrow{50}$ I | Example 31 | 41 |
| " | | —(CH$_2$)$_5$— | 0 | 0 | " | $S_1$ $\xrightarrow{-15}$ Sc $\xrightarrow{45}$ $S_A$ $\xrightarrow{60}$ I | Example 31 | 42 |
| —(CH$_2$)$_3$O$C_2H_5$ | | " | 0 | 0 | (CH$_2$)$_3$O$C_2H_5$ | $S_1$ $\xrightarrow{-20}$ Sc $\xrightarrow{60}$ I | Example 31 | 43 |
| —$\overset{F}{\underset{*}{C}}HC_5H_{11}$ | +1.1° | — | — | — | — | — | Example 34 | 44 |
| —$\overset{CH_3}{\underset{*}{C}}HC_2H_5$ (S) | +0.5° | — | — | — | — | — | Example 34 | 45 |

TABLE 7-continued

| | | | | | | | |
|---|---|---|---|---|---|---|---|
| C₃H₇ | | — | — — — | — | Example 33 | 46 |
| " | | — | — — — | — | Example 33 | 47 |
| " | | — | — — — | — | Example 33 | 48 |
| —CH₂CH(CH₃)C₂H₅ * (S) | −0.5° | -(CH₂)₄- | 0   0 | —CH₂CH(CH₃)C₂H₅ * (S) | −0.5 | Example 31 | 49 |
| C₄H₉ | $S_2 \xrightarrow{-16} S_1 \xrightarrow{8} Sc^* \xrightarrow{44} I$ | — | — — — | — | Example 31 | 50 |
| " | $S_1 \xrightarrow{12} I$, $\xleftarrow{-23.5} Sc^* \xleftarrow{0.5} S_A \xleftarrow{2.5}$ | — | — — — | — | Example 31 | 51 |
| C₃H₇ | $S_1 \xrightarrow{9} Sc^* \xrightarrow{46} I$ | — | — — — | — | Example 31 | 52 |
| " | | — | — — — | — | Example 31 | 53 |
| " | | — | — — — | — | Example 31 | 54 |
| " | −0.9° | — | — — — | — | Example 31 | 55 |
| " | | — | — — — | — | Example 31 | 56 |
| -(CH₂)₄OC₂H₅ | −1.1° | — | — — — | — | Example 31 | 57 |
| -(CH₂)₄OC₂H₅ | −0.5° | — | — — — | — | Example 31 | 58 |
| CH₃ | −0.6° | — | — — — | — | Example 31 | 59 |
| CH₃ | −0.5° | — | — — — | — | Example 31 | 60 |
| " | −0.5° | — | — — — | — | Example 31 | 61 |
| C₃H₇ | | — | — — — | — | Example 31 | 62 |
| C₈H₁₇ | −0.9° | — | — — — | — | Example 31 | 63 |

TABLE 7-continued

| | | | | | | |
|---|---|---|---|---|---|---|
| $C_3H_7$ | — | — | — — — | — | 31 Example 31 | 64 |
| $CH_3$ | $K \xrightarrow{45} I$ <br> $\xleftarrow{-2} Sc^* \xleftarrow{30} S_A \xleftarrow{33}$ | — | — — — | — | Example 31 | 65 |
| $CH_3$ | $S_A \xrightarrow{-26} S_1 \xrightarrow{-10} Sc^* \xrightarrow{18} I$ | — | — — — | — | Example 31 | 66 |
| " | $K - S \xrightarrow{-8} Sc^* \xrightarrow{25} I$ | — | — — — | — | Example 31 | 67 |

Example 68

A liquid crystal composition was prepared by using the liquid crystal compounds. Preparation was performed by placing weighed amounts of the specified compounds in a sample bottle and mixing the compounds while melting them by heating.

Production of liquid crystal element

A polyimide polymer film was formed on each of a pair of glass substrates provided with transparent electrodes of indium oxide, and the film-coated substrates were rubbed in a given direction by using a gauze, with glass fiber (5 μm in diameter) disposed as spacer so that rubbing of the two substrates would be made parallel to each other, thereby constituting a liquid crystal cell, and the previously prepared liquid crystal composition was vacuum encapsulated in said liquid crystal cell to form a liquid crystal element.

This liquid crystal element was combined with a polarizer and an electric field of 20 V was applied thereto, observing the change in strength of transmitted light. It was ascertained that said liquid crystal element can be used as a switching element.

TABLE 8

| Example No. | Liquid crystal composition | Actually measured value of spontaneous polarization* |
|---|---|---|
| 68 | Compound of Example 43 <br> 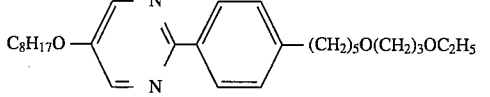 <br> 10 wt % <br><br> Compound of Example 38 <br> 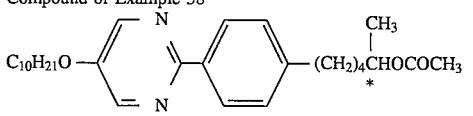 <br> 20 wt % <br><br> 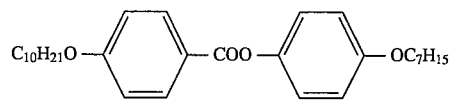 <br> (known compound)     70 wt % | 11 nc/cm² <br> (T − Tc = −10° C.) |

*Measured according to Sawyer-Tower's method

The values of spontaneous polarization and response time achievable with the compounds of this invention were determined. The results are shown in Table 9.

TABLE 9

| | Spontaneous polarization | | |
|---|---|---|---|
| Compound | (nC/cm²) | (Temp. at the the time of measurement) | Response time* (μs) |
| Example 35 | 18 | (9° C.) | 154 (20° C.) |

TABLE 9-continued

| Compound | (nC/cm²) | Spontaneous polarization (Temp. at the the time of measurement) | Response time* (µs) |
|---|---|---|---|
| Hydrogenated compound of Example 35 | 79 | (0° C.) | 27 (20° C.) |
| Example 36 (Hydrogenated compound) | 23 | (15° C.) | 59 (20° C.) |
| Example 50 | 23 | (20° C.) | 40 (20° C.) |
| Example 52 | 9 | (12.4° C.) | 70 (20° C.) |

*Calculated from full width at half maximum of polarization inversion current. The figures in the parentheses are temperature at the time of measurement.

What we claim is:

1. Phenylpyrimidine derivatives represented by the general formula I:

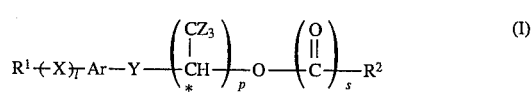

wherein $R^1$ is an alkyl group having 3–20 carbon atoms; $R^2$ is an alkyl group having 1–20 carbon atoms or an alkoxyalkyl group having 2–20 carbon atoms, which may be substituted with a halogen atom; X is —O—, —COO— or —OCO—; Ar is

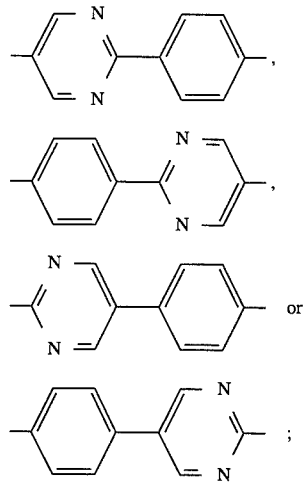

Y is —(CH$_2$)$_{\overline{m}}$ or —CH=CH—(CH$_2$)$_{\overline{n}}$; Z is a hydrogen or fluorine atom and * denotes an asymmetric carbon atom; m is an integer of 0 to 10; n is an integer of 0 to 8; l and p are each a number of 0 or 1; and s is a number of 0 or 1; with the provisos that:

when s is 1, Z is a fluorine atom or Y is —CH=CH—(CH$_2$)$_{\overline{n}}$ or p is 0;

when both p and s are 0, Y is —CH=CH—(CH$_2$)$_{\overline{n}}$;

when p is 0, m is an integer of 2 to 10 and n is an integer of 1 to 8; and when p is 1 and Z is a hydrogen atom, m is an integer of 1 to 10.

2. The phenylpyrimidine derivatives according to claim 1, wherein Z is hydrogen atom.

3. The phenylpyrimidine derivatives according to claim 1, wherein Z is fluorine atom.

4. The phenylpyrimidine derivatives according to claim 1, wherein Z is hydrogen atom, Y is —(CH$_2$)$_{\overline{m}}$, p is 1 and s is 0.

5. The phenylpyrimidine derivatives according to claim 1, wherein Z is fluorine atom, Y is —(CH$_2$)$_{\overline{m}}$, p is 1 and s is 0.

6. The phenylpyrimidine derivatives according to claim 1, wherein Z is fluorine atom, Y is —(CH$_2$)$_{\overline{m}}$, p is 1 and s is 1.

7. The phenylpyrimidine derivatives according to claim 1, wherein p is 0 and $R^2$ is an alkoxyalkyl group having 2 to 20 carbon atoms.

8. The phenylpyrimidine derivatives according to claim 1, wherein p is 0, Y is —(CH$_2$)$_{\overline{m}}$, and m is an integer of 3 to 10.

9. The phenylpyrimidine derivatives according to claim 1, wherein Y is —CH=CH—(CH$_2$)$_{\overline{n}}$.

10. The phenylpyrimidine derivatives according to claim 1, wherein Z is hydrogen atom, Y is —(CH$_2$)$_{\overline{m}}$, p is 1, s is 0, and Ar is

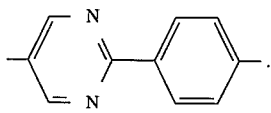

11. The phenylpyrimidine derivatives according to claim 1, wherein Z is fluorine atom, Y is —(CH$_2$)$_{\overline{m}}$, p is 1, s is 0 and Ar is

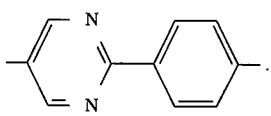

12. The phenylpyrimidine derivatives according to claim 1, wherein p is 1,

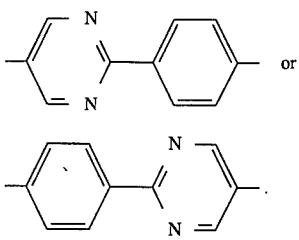

13. The phenylpyrimidine derivatives according to claim 12, wherein s is 0 and Ar is

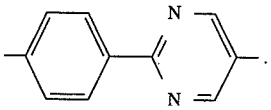

14. The phenylpyrimidine derivatives according to claim 13, wherein Z is a hydrogen atom.

15. The phenylpyrimidine derivatives according to claim 1, wherein s is 1 and p is 0.

16. The phenylpyrimidine derivatives according to claim 1, wherein s is 1 and Y is —CH=CH—(CH$_2$)$_{\overline{n}}$.

17. The phenylpyrimidine derivatives according to claim 1, wherein p is 0, is 0 and Y is —CH=CH—(CH$_2$)$_{\overline{n}}$.

* * * * *